United States Patent
Sato et al.

(10) Patent No.: US 8,868,174 B2
(45) Date of Patent: Oct. 21, 2014

(54) BRAIN INFORMATION OUTPUT APPARATUS, ROBOT, AND BRAIN INFORMATION OUTPUT METHOD

(75) Inventors: Masaaki Sato, Kyoto (JP); Takahito Tamagawa, Kyoto (JP); Okito Yamashita, Kyoto (JP); Yusuke Takeda, Kyoto (JP); Mitsuo Kawato, Kyoto (JP); Kentaro Yamada, Wako (JP); Masahiro Kimura, Wako (JP); Akihiro Toda, Wako (JP); Tatsuya Okabe, Wako (JP)

(73) Assignees: Honda Motor Co., Ltd., Tokyo (JP); Advanced Telecommunications Research Institute International, Kyoto (JP)

( * ) Notice: Subject to any disclaimer, the term of this patent is extended or adjusted under 35 U.S.C. 154(b) by 445 days.

(21) Appl. No.: 13/202,784
(22) PCT Filed: Feb. 22, 2010
(86) PCT No.: PCT/JP2010/052631
§ 371 (c)(1), (2), (4) Date: Oct. 26, 2011
(87) PCT Pub. No.: WO2010/098284
PCT Pub. Date: Sep. 2, 2010

(65) Prior Publication Data
US 2012/0035765 A1 Feb. 9, 2012

(30) Foreign Application Priority Data
Feb. 24, 2009 (JP) .................................. 2009-041338

(51) Int. Cl.
A61B 5/04 (2006.01)
B25J 13/00 (2006.01)
(Continued)

(52) U.S. Cl.
CPC ............... *B25J 13/00* (2013.01); *A61B 5/0073* (2013.01); *A61B 5/0059* (2013.01); *G06F 3/015* (2013.01)
(Continued)

(58) Field of Classification Search
USPC .................... 600/544, 545; 700/264
See application file for complete search history.

(56) References Cited

U.S. PATENT DOCUMENTS

2005/0228515 A1* 10/2005 Musallam et al. ............... 700/83
2006/0074822 A1* 4/2006 Eda et al. ......................... 706/14
(Continued)

FOREIGN PATENT DOCUMENTS

JP 2004-180817 A 7/2004
JP 2008-178546 A 8/2008

OTHER PUBLICATIONS

Office Action from Japanese Patent App. No. 2009-041338 (Jun. 14, 2013) with partial English translation.
(Continued)

*Primary Examiner* — Etsub Berhanu
(74) *Attorney, Agent, or Firm* — Cermak Nakajima McGowan LLP; Tomoko Nakajima

(57) ABSTRACT

A brain information output apparatus includes an intention determination information storage unit in which two or more pieces of intention determination information can be stored, with each intention determination information including a pair of an intention identifier, and a learning feature amount group including one or more feature amounts extracted from second learning data that is obtained by converting first learning data into intracerebral brain activity data, the first leaning data being acquired from the outside of the cranium of a user when the user performs a trial according to one intention; a first brain activity data acquiring unit that acquires first brain activity data from the outside of the cranium of a user; a second brain activity data acquiring unit that converts the first brain activity data to intracerebral brain activity data, and acquires second brain activity data; a feature amount group acquiring unit that acquires, from the second brain activity data, an input feature amount group including one or more feature amounts; an intention identifier acquiring unit that acquires an intention identifier corresponding to the input feature amount group based on the two or more pieces of intention determination information; and an intention identifier output unit that outputs the intention identifier.

7 Claims, 30 Drawing Sheets

(51) Int. Cl.
  *G06F 3/01* (2006.01)
  *G06N 99/00* (2010.01)
  *A61B 5/0476* (2006.01)
  *A61B 5/00* (2006.01)
  *A61B 5/055* (2006.01)

(52) U.S. Cl.
  CPC ...... (2013.01); *A61B 5/4064* (2013.01); *A61B 5/6814* (2013.01); *G06N 99/005* (2013.01); *A61B 5/0476* (2013.01); *A61B 5/055* (2013.01)
  USPC .......................................... 600/545; 600/473

(56) References Cited

U.S. PATENT DOCUMENTS

2008/0140149 A1* 6/2008 John et al. ...................... 607/45
2008/0249430 A1* 10/2008 John et al. ..................... 600/544

OTHER PUBLICATIONS

International Search Report for PCT Patent App. No. PCT/JP2010/052631 (Apr. 6, 2010).

"Toward Brain-Computer Interfacing," eds. Dornhege, G., et al., 2007, pp. 1-25, The MIT Press, Cambridge, MA, US, ISBN 978-0262042444.

* cited by examiner

FIG.14

| | Subject1 | Subject2 |
|---|---|---|
| LEFT HAND | Gearshift of automobile<br>Command is sent to the shoulder to the finger tips.<br>Motion of arm may be perceived in some cases. | Image of raising arm high and hitting something. |
| RIGHT HAND | Bend elbow to right angle, and turn arm 90 degrees from the right side to the front, without providing space between upper arm and body<br>Command is sent to the shoulder to the finger tips.<br>Motion of arm may be perceived in some cases. | Image of playing keyboard instrument.<br>Play a wide range with arms, not just with fingers.<br>Imagine sound along with motion. |
| TONGUE | Feel top wall inside mouth with central portion of tongue.<br>Command is sent to portion near uvula.<br>There is strong sensation that inside of the mouth is touched in some cases. | Image of moving tongue to lick a distant object. |
| FOOT | Running<br>Imagine rotating stationary pelvis like bicycle pedal.<br>Command is sent from the central portion of pelvis to the buttock.<br>In some cases, it may be perceived that right and left feet alternately rotate largely. | Imagine sending different commands to thighs and calves of legs, while keeping balance as in turn of ski.<br>There is sensation that something is pushing back from the bottom of feet. |

FIG.22

|  |  | Day1 | Day2 | Day3 | Day4 | Day5 | Day6 | Day7 | Day8 | Day9 | Mean |
|---|---|---|---|---|---|---|---|---|---|---|---|
| Estimated current | correct rate(%) | 62.85 | 71.43 | 73.57 | 67.14 | 72.85 | 63.57 | 85.71 | 74.28 | 84.28 | 72.85 |
|  | kappa value | 0.50 | 0.61 | 0.64 | 0.56 | 0.63 | 0.51 | 0.80 | 0.65 | 0.79 | 0.63 |
|  | SD | 14.91 | 8.14 | 8.01 | 5.24 | 11.64 | 5.24 | 3.19 | 4.73 | 6.62 | 7.52 |
| Scalp brain wave | correct rate(%) | 62.85 | 73.57 | 67.14 | 71.43 | 70.00 | 49.28 | 68.57 | 67.85 | 71.08 | 66.86 |
|  | kappa value | 0.50 | 0.64 | 0.56 | 0.61 | 0.60 | 0.32 | 0.58 | 0.57 | 0.61 | 0.55 |
|  | SD | 4.84 | 12.07 | 5.71 | 9.31 | 4.84 | 7.62 | 6.54 | 9.03 | 9.78 | 7.74 |

FIG.24

|  | | Day1 | Day2 | Day3 | Day4 | Day5 | Mean |
|---|---|---|---|---|---|---|---|
| estimated current | correct rate (%) | 78.50% | 60.00% | 65.00% | 65.71% | 73.00% | 68.44% |
|  | kappa value | 0.71 | 0.47 | 0.53 | 0.54 | 0.64 | 0.58 |
|  | SD | 10.80 | 7.63 | 7.28 | 5.80 | 7.30 | 7.76 |
| EEG | correct rate (%) | 73.50% | 40.70% | 47.00% | 60.70% | 45.00% | 53.38% |
|  | kappa value | 0.65 | 0.21 | 0.29 | 0.48 | 0.27 | 0.38 |
|  | SD | 7.69 | 6.62 | 7.95 | 9.84 | 6.60 | 7.74 |

FIG.28

|  |  | Day1 | Day2 | Day3 | Day4 | Day5 | Day6 | Day7 | Day8 | Mean±SD |
|---|---|---|---|---|---|---|---|---|---|---|
| 5run 140trial | correct rate (%) | 69.99 | 79.99 | 50.00 | 65.00 | 64.14 | 82.85 | 68.56 | 52.14 | 66.58±11.66 |
|  | kappa value | 0.59 | 0.73 | 0.33 | 0.53 | 0.52 | 0.77 | 0.58 | 0.36 | 0.55±0.15 |
| 8run 224trial | correct rate (%) | 65.00 | 75.00 | 68.75 | 67.14 | 82.14 | 82.14 | 65.00 | 60.00 | 70.64±8.24 |
|  | kappa value | 0.53 | 0.66 | 0.58 | 0.56 | 0.76 | 0.76 | 0.53 | 0.46 | 0.6±0.11 |
| 10run 280trial | correct rate (%) | 79.99 | 85.00 | 75.00 | 72.80 | 80.00 | 83.50 | 87.10 | 85.50 | 81.11±5.13 |
|  | kappa value | 0.73 | 0.80 | 0.66 | 0.63 | 0.73 | 0.78 | 0.82 | 0.80 | 0.74±0.06 |

US 8,868,174 B2

BRAIN INFORMATION OUTPUT APPARATUS, ROBOT, AND BRAIN INFORMATION OUTPUT METHOD

This application is a national phase entry under 35 U.S.C. §371 of PCT Patent Application No. PCT/JP2010/052631, filed on Feb. 22, 2010, which claims priority under 35 U.S.C. §119 to Japanese Patent Application No. 2009-041338, filed Feb. 24, 2009, both of which are incorporated by reference.

TECHNICAL FIELD

The present invention relates to a brain information output apparatus and the like that output brain information.

BACKGROUND ART

Due to recent accumulation of physiological knowledge about brain, development in encephalometers, decrease in the cost of high-performance computers, and progression in the field of machine learning and the like, research on Brain Machine Interface (BMI) has been attracting a larger attention (Non-Patent Document 1). "BMI" is an interface connecting brain and machine. BMI measures brain activity signals generated when a person is thinking, or taking a certain action, and picks up an intention of a user by performing signal processing on the measured data.

[Non-Patent Document 1] Toward Brain-Computer Interfacing (Neural Information Processing), MIT Press, ISBN 978-0262042444

DISCLOSURE OF INVENTION

Problem To be Solved by the Invention

However, with conventional BMIs, intention determination is performed using brain activity data acquired from the outside of the cranium as is, and therefore it has been difficult to perform intention determination with high accuracy.

That is, in brain waves measured at the scalp, the brain potential has been shunted or attenuated during transmission, and thus it is difficult to determine the signal source or the brain activity performed at the signal source based only on the information obtained at the sensor positions. Therefore, in the case where brain waves measured at the scalp are used as is, it has not been easy to perform intention determination with high accuracy.

Means for Solving the Problems

A first aspect of the present invention is directed to a brain information output apparatus including: an intention determination information storage unit in which two or more pieces of intention determination information can be stored, each intention determination information including a pair of an intention identifier that is information for identifying an intention of a user, and a learning feature amount group including one or more feature amounts extracted from second learning data that is obtained by converting first learning data into intracerebral brain activity data, the first leaning data being data of a brain activity acquired from the outside of the cranium of a user when the user performs a trial, which is a series of actions, according to an intention identified by the intention identifier; a first brain activity data acquiring unit that acquires first brain activity data, which is data of a brain activity, from the outside of the cranium of a user; a second brain activity data acquiring unit that converts the first brain activity data acquired from the outside of the cranium of a user to intracerebral brain activity data, and acquires second brain activity data; a feature amount group acquiring unit that acquires, from the second brain activity data, an input feature amount group including one or more feature amounts; an intention identifier acquiring unit that acquires an intention identifier corresponding to the input feature amount group based on the two or more pieces of intention determination information stored in the intention determination information storage unit; and an intention identifier output unit that outputs the intention identifier acquired by the intention identifier acquiring unit.

With such a configuration, brain activity data acquired from the outside of the cranium is converted to intracerebral brain activity data and used, and thereby intention determination can be performed with high accuracy.

A second aspect of the present invention is directed to a brain information output apparatus further including: a first learning data acquiring unit that acquires, when a user performs a trial, which is a series of actions, according to one intention, first learning data, which is time-series data indicating a brain activity, from the brain of the user using one or more sensors, for each of the sensors; a second learning data acquiring unit that converts the first learning data acquired from the outside of the cranium of a user to data of an intracerebral brain activity, and acquires second learning data; a learning feature amount group acquiring unit that acquires, from the second learning data, a learning feature amount group including one or more feature amounts; and an intention determination information accumulation unit that accumulates, in the intention determination information storage unit, intention determination information including the second learning feature amount group and the intention identifier for identifying the one intention.

With such a configuration, brain activity data acquired from the outside of the cranium is converted to intracerebral brain activity data and used, and thereby intention determination can be performed with high accuracy. Also, it is possible to acquire learning data automatically.

Also, a third aspect of the present invention is directed to, with respect to the first aspect of the present invention, a brain information output apparatus wherein the second brain activity data acquiring unit acquires second brain activity data by applying the hierarchical variational Bayes approach to the first brain activity data.

With such a configuration, brain activity data acquired from the outside of the cranium is converted to intracerebral brain activity data and used, and thereby intention determination can be performed with high accuracy.

Also, a fourth aspect of the present invention is directed to, with respect to a first or second aspect of the present invention, a brain information output apparatus wherein the intention identifier acquiring unit includes: a probability calculation section that calculates a probability that the input feature amount group acquired by the feature amount group acquiring unit corresponds to each of two or more intention identifiers included in the two or more pieces of intention determination information in the intention determination information storage unit, using the two or more pieces of intention determination information, for each of the two or more intention identifiers; and an intention identifier acquiring section that acquires an intention identifier that corresponds to a largest probability based on the probabilities of the intention identifiers calculated by the probability calculation section.

With such a configuration, brain activity data acquired from the outside of the cranium is converted to intracerebral brain activity data and used, and thereby intention determination can be performed with high accuracy.

Effect of the Invention

With the brain information output apparatus of the present invention, it is possible to perform intention determination with high accuracy.

BEST MODE FOR CARRYING OUT THE INVENTION

Hereinafter, embodiments of a brain information output apparatus and the like will be described with reference to the drawings. Note that elements assigned the same reference numerals in the embodiments perform the same operations, and thus such elements may not be repetitively described.

Embodiment 1

In the present embodiment, a brain information output apparatus will be described that converts first brain activity data that has been acquired from the outside of the cranium to second brain activity data (intracerebral brain activity data), and detects an intention by using the second brain activity data.

Furthermore, in the present embodiment, a description will be also given to a robot system that includes a robot that operates in response to outputs from the brain information output apparatus.

FIG. 1 is a conceptual diagram of a robot system 1 of the present embodiment. The robot system 1 includes a brain information output apparatus 11 and a robot 12. The brain information output apparatus 11 acquires brain information from a user, detects an intention of the user, and outputs an intention identifier indicating the intention to the robot 12. Also, the robot 12 is an electronic device that receives an intention identifier from the brain information output apparatus 11, and performs an operation corresponding to the intention identifier. The robot 12 may be an electronic device having a human form, or may have other forms. The robot 12 may be, for example, a moving body such as a four-wheel car, a two-wheel car, an aircraft, or a train.

FIG. 2 is a block diagram of the robot system 1 according to the present embodiment. The brain information output apparatus 11 constituting the robot system 1 includes an intention determination information storage unit 111, a first learning data acquiring unit 112, a second learning data acquiring unit 113, a learning feature amount group acquiring unit 114, an intention determination information accumulating unit 115, a first brain activity data acquiring unit 116, a second brain activity data acquiring unit 117, a feature amount group acquiring unit 118, an intention identifier acquiring unit 119 and an intention identifier output unit 120.

The intention identifier acquiring unit 119 includes a probability calculation section 1191 and an intention identifier acquiring section 1192.

The robot 12 includes an operation information storage unit 121 and an intention identifier accepting unit 122 and an execution unit 123.

Two or more pieces of intention determination information can be stored in the intention determination information storage unit 111. The intention determination information includes an intention identifier and a learning feature amount group. The intention identifier is information for identifying an intention of a user. The learning feature amount group is one or more feature amounts extracted from second learning data. The second learning data is data obtained by converting first learning data that is brain activity data acquired from the outside of the cranium of a user, when the user has performed a trial, which is a series of actions, according to the intention identified by an intention identifier, to intracerebral brain activity data. Here, "intention" refers to an action that is reflected in the brain activity of the user, for example, moving part of the body (e.g., right hand, left hand, tongue, or foot), or imagining a certain state (e.g., moving a right hand, sticking his or her tongue, or running). Also, the intention identifier identifies a part of the body that the user moves, for example, and four intention identifiers, "right hand", "left hand", "tongue" and "foot", can be used for example. Also, two intention identifiers, "right hand" and "left hand", may be used. Although there is no restriction to the number of the intention identifiers, it is generally considered that the smaller the number of the intention identifiers is, the higher the possibility that the intention identifier output by the brain information output apparatus 11 matches the intention of the user is. The learning feature amount group refers to information on one or more feature amounts extracted from learning data. The learning data is data acquired from the brain of a user when the user has performed a series of actions according to the intention identified by the intention identifier. The learning data may be any data as long as it indicates a brain activity and is acquired from the brain, such as data acquired with by NIRS (near-infrared spectrophotometry), fMRI (functional MRI), MEG (magneto-encephalograph), EEG (electroencephalograph). Also, "intracerebral" used herein includes the brain surface.

Although the intention determination information storage unit 111 preferably is a non-volatile recording medium, the intention determination information storage unit 111 can be realized also by a volatile recording medium.

There is no restriction to the process by which intention determination information is stored in the intention determination information storage unit 111. For example, intention determination information may be stored in the intention determination information storage unit 111 via a recording medium, or intention determination information sent via a communication line or the like may be stored in the intention determination information storage unit 111. Alternatively, intention determination information input via an input device may be stored in the intention determination information storage unit 111.

The first learning data acquiring unit 112 acquires the first learning data from the outside of the cranium of the user. The first learning data is time-series data indicating a brain activity that is acquired from the outside of the cranium of a user using each of one or more sensors, when the user has performed a trial, which is a series of actions, according to one intention. The first learning data acquiring unit 112 is generally a brain wave measuring apparatus. That is the first learning data is brain wave data.

The second learning data acquiring unit 113 converts the first learning data acquired from the outside of the cranium of a user to intracerebral brain activity data, and thereby acquires second learning data. The second learning data acquiring unit 113 acquires the second learning data based on the first learning data by using hierarchical variational Bayes approach. Specifically, the second learning data acquiring unit 113 sets a first region where the space-time distribution of intracerebral current sources is estimated with a first resolution and a second region where the space-time distribution is estimated with a second resolution that is lower than the first resolution, and estimates the space-time distributions of the current sources in the set first and second regions based on the electric phenomenon observed from the outside of the cranium of the user. By distributing parameters concentrated in a region where highly accurate estimation is desired, reduction in estimation accuracy due to increased parameters can be prevented.

More specifically, for example, the second learning data acquiring unit 113 converts first learning data and thereby obtains second learning data through Expression 1 to Expression 9 indicated below.

$$E = G \cdot J + \xi \quad \text{[Expression 1]}$$

In Expression 1, "G" is a lead field matrix, "J" is an intracerebral current distribution, and "$\xi$" is a noise. "E" is an electric field measured by a sensor placed on the scalp. The lead field matrix G is calculated by an electromagnetic field analysis technique described below, and "G·J" expresses an electric field generated at a sensor position on the scalp due to the intracerebral current distribution J. Expression 1 is an expression for calculating an electric field E, which is the result, from the intracerebral current distribution J, which is the cause, and this is called a direct problem. However, now it is the electric field E that is measured and it is the intracerebral current distribution J that needs to be estimated by calculation, and thus it is necessary to obtain the cause from the result; this is commonly called an inverse problem. The second learning data acquiring unit 113 performs processing for solving an inverse problem in which the second learning data (namely, J) is obtained from the first learning data (namely, E).

Hereinafter, a specific calculation flow of the second learning data acquiring unit 113 will be described.

The probability (model probability) that the electric field E is observed when the current distribution J is applied is set by Expression 2.

$$P(E \mid J, \sigma) = \quad \text{[Expression 2]}$$
$$\prod_{t=1}^{T} N_D(E(t) \mid G \cdot J(t), \Sigma_G^{-1}) \text{ where } \Sigma_G = \text{diag}(\sigma)$$

Here, "$\sigma$" is a standard deviation when noise measured by the respective sensors is assumed to be Gaussian noise. Specifically, Expression 2 indicates the probability of the electric field E when the current distribution J and the standard deviation $\sigma$ of the noise are applied. Also, "ND" indicates the normal distribution, and can be expressed by Expression 3 when an arbitrary parameter is X, an expectation value for that parameter is X-bar, and a covariance matrix is $\Sigma^{-1}$.

$$N_D\left(X \mid \overline{X}, \sum^{-1}\right) \equiv \quad \text{[Expression 3]}$$
$$\exp\left[-\frac{1}{2}(X - \overline{X})'\Sigma(X - \overline{X}) + \frac{1}{2}\log|\Sigma| + \frac{N}{2}\log\left(\frac{1}{2\pi}\right)\right]$$

Along with the preparations as described above, a hierarchical prior distribution expressed by Expression 4 is set with respect to the current distribution J prior to observation of the electric field E. Here, "$\alpha J$" is a parameter indicating the variance of the current distribution J, and "$\alpha Z$" is a parameter indicating the variance of an action current Z. In addition, "$\Gamma$" indicates a gamma distribution, "$Y^J$" indicates a degree of freedom of the gamma distribution of the current distribution J, and "$Y^Z$" indicates a degree of freedom of the gamma distribution of the action current Z.

$$P_0(J \mid Z, \alpha_J) = \quad \text{[Expression 4]}$$
$$\prod_{t=1}^{T} N_D(J(t) \mid W \cdot Z(t), A_J^{-1}) \text{ wherein } A_J = \text{diag}(\alpha_J)$$
$$P_0(Z \mid \alpha_Z) = \prod_{t=1}^{T} N_D(Z(t) \mid 0, A_Z^{-1}) \text{ wherein } A_Z = \text{diag}(\alpha_Z)$$
$$P_0(\alpha_J) = \Gamma(\alpha_J \mid \overline{\alpha}_{J0}, \gamma_{J0})$$
$$P_0(\alpha_Z) = \Gamma(\alpha_Z \mid \overline{\alpha}_{Z0}, \gamma_{Z0})$$
$$P_0(\sigma) = 1/\sigma$$

In the case where the aforementioned probability model (Expression 2) and hierarchical prior distribution (Expression 4) are applied, it is generally not possible to analytically obtain a marginal likelihood of the model, and thus the marginal likelihood of the model is approximately calculated with the use of hierarchical variational Bayes approach. Then, posterior distribution is introduced to each of the current distribution and the variance thereof. Note that the second learning data acquiring unit 113 alternately repeats estimation of the current distribution and estimation of the current variance, until a free energy F described below converges. Here, "convergence" is deemed to be achieved when a change in the free energy F has become smaller than a predetermined value.

A posterior distribution Q (J, Z) with respect to the current distribution can be calculated according to Expression 5, and parameters in Expression 5 are updated according to Expression 6.

$$\log Q(J, Z) = \langle \log P(E, \{J\}, \{\alpha\}) \rangle_\alpha + \text{const} \quad \text{[Expression 5]}$$
$$= -\frac{1}{2}(E - G \cdot J)' \Sigma_G (E - G \cdot J) -$$
$$\frac{1}{2}(J - W \cdot Z)' A_J (J - W \cdot Z) - \frac{1}{2} Z' A_Z Z + \text{const}$$
$$= -\frac{1}{2}(J - \overline{J}) \Sigma_{JJ} (J - \overline{J}) - \frac{1}{2}(Z - \overline{Z}) \Sigma_{ZZ} (Z - \overline{Z}) +$$
$$(Z - \overline{Z}) \Sigma_{ZJ} (J - \overline{J}) + \text{const}$$
$$= -\frac{1}{2}(J - \overline{J}) \Sigma_J (J - \overline{J}) - \frac{1}{2}[(Z - \overline{Z}) - R_Z (J - \overline{J})] \cdot$$
$$\Sigma_{ZZ} \cdot [(Z - \overline{Z}) - R_Z (J - \overline{J})] + \text{const}$$

where $$\Sigma_{JJ} = G'\Sigma_G G + A_J$$
$$\Sigma_{ZZ} = W'A_J W + A_Z$$
$$\Sigma_{ZJ} = \Sigma_{ZZ} \cdot R_Z = W' \cdot A_J$$
$$\Sigma_J = \Sigma_{JJ} - R'_Z \Sigma_{ZZ} R_Z = G'\Sigma_G G + \Sigma_\alpha^{-1}$$
$$R_Z = \Sigma_{ZZ}^{-1} \cdot W' \cdot A_J$$

$$\bar{J} = \Sigma_\alpha G \cdot \Sigma_E^{-1} \cdot E$$
$$\bar{Z} = A_Z^{-1}(G \cdot W) \cdot \Sigma_E^{-1} \cdot E$$

where $$\Sigma_\alpha = W A_Z^{-1} W' + A_J^{-1}$$

$$\Sigma_E = G\Sigma_\alpha G' + \Sigma_G^{-1} = (G \cdot W) A_Z^{-1} (G \cdot W)' +$$
$$G \cdot A_J^{-1} \cdot G' + \Sigma_G^{-1}$$
$$= (G \cdot W) A_Z^{-1} (G \cdot W)' + \sum_{r=1}^{N_R} \alpha_J^{-1}(r)(G \cdot X_r^{-1} \cdot G') + \Sigma_G^{-1}$$

[Expression 6]

The posterior distribution $Q(\alpha J, \alpha Z, \sigma)$ with respect to the variance of the current distribution can be calculated according to in Expression 7. Also, parameters in Expression 7 are updated according to Expression 8.

$$\log Q(\alpha_J, \alpha_Z, \sigma) = \langle \log P(E, \{J\}, \{\alpha\}) \rangle_J + const$$

$$= -\frac{1}{2} \left\langle \begin{bmatrix} (E - G \cdot J)'\Sigma_G(E - G \cdot J) + \\ (J - W \cdot Z)'A_J(J - W \cdot Z) + \\ Z'A_Z \cdot Z \end{bmatrix} \right\rangle_J -$$

$$\gamma_{J0}\overline{\alpha}_{J0}^{-1}\alpha_J - \gamma_{Z0}\overline{\alpha}_{Z0}^{-1}\alpha_Z + \frac{T}{2}[\log|\Sigma_G| +$$
$$\log|A_J| + \log|A_Z|] + (\gamma_{J0} - 1)\log\alpha_J +$$
$$(\gamma_{Z0} - 1)\log\alpha_Z - \log\sigma + const$$
$$= [(\gamma_\sigma - 1)\log\sigma - \gamma_\sigma \overline{\sigma}^{-1}\sigma] +$$
$$[(\gamma_J - 1)\log\alpha_J - \gamma_J \overline{\alpha}_J^{-1}\alpha_J] +$$
$$[(\gamma_Z - 1)\log\alpha_Z - \gamma_Z \overline{\alpha}_Z^{-1}\alpha_Z] + const$$

[Expression 7]

$$\gamma_\sigma(s) = \frac{T}{2} \cdot N(s)$$

$$\gamma_\sigma(s) \cdot \overline{\sigma}^{-1}(s) = \frac{1}{2}(\Delta_E(s) + \langle \Delta E^2(s) \rangle)$$

$$\gamma_J(r) = \frac{T}{2} \cdot N_J(r) + \gamma_{J0}$$

$$\gamma_J(r)\overline{\alpha}_J^{-1}(r) = \frac{1}{2}(\Delta_J(r) + \langle \Delta J^2(r) \rangle) + \gamma_{J0}\overline{\alpha}_{J0}^{-1}$$

$$\gamma_Z = \frac{T}{2} + \gamma_{Z0}$$

$$\gamma_Z \overline{\alpha}_Z^{-1} = \frac{1}{2}(\Delta_Z + \langle \Delta Z^2 \rangle) + \gamma_{Z0}\overline{\alpha}_{Z0}^{-1}$$

[Expression 8]

The aforementioned free energy F is calculated according to Expression 9.

$$F = L + H_\sigma + H_{\alpha J} + H_{\alpha Z} + L_0 \qquad \text{[Expression 9]}$$

In the above expression.

$$L = -\frac{T}{2}\log|\Sigma_E| - \frac{1}{2}(E_E + E_J + E_Z) \text{ where}$$

-continued $$E_E \equiv \sum_s \sigma(s)[\Delta_E(s) + \langle \Delta E^2(s) \rangle]$$

$$E_J \equiv \sum_r \alpha_J(r)[\Delta_J(r) + \langle \Delta J^2(r) \rangle]$$

$$E_Z \equiv \sum_i \alpha_Z(i)[\Delta_Z(i) + \langle \Delta Z^2(i) \rangle]$$

$$H_\sigma = \langle \log(P_0(\sigma)/Q(\sigma)) \rangle = \sum_s H_G(\gamma_\sigma(s)) \text{ where}$$

$$H_G(\gamma) \equiv \log\Gamma(\gamma) - \gamma\psi(\gamma) + \gamma$$

$$H_{\alpha J} = \langle \log(P_0(\alpha_J)/0(\alpha_J)) \rangle$$

$$= \sum_r \begin{bmatrix} \gamma_{J0}(\log(\alpha_J(r)/\alpha_{J0}) - \\ (\alpha_J(r)/\alpha_{J0}) + 1) + \\ H_G(\gamma_J(r)) + H_{G0}(\gamma_J(r) \cdot \gamma_{J0}) \end{bmatrix}$$

$$H_{\alpha Z} = \langle \log(P_0(\alpha_Z)/0(\alpha_Z)) \rangle$$

$$= \sum_i \begin{bmatrix} \gamma_{Z0}(\log(\alpha_Z(i)/\alpha_{Z0}) - \\ (\alpha_Z(i)/\alpha_{Z0}) + 1) + \\ H_G(\gamma_Z(i)) + H_{G0}(\gamma_Z(i) \cdot \gamma_{Z0}) \end{bmatrix}$$

where $$H_{G0}(\gamma, \gamma_0) \equiv$$
$$-[\log\Gamma(\gamma_0) - \gamma_0 \log\gamma_0 + \gamma_0] + \gamma_0(\psi(\gamma) - \log\gamma)$$

$$L_0 = \frac{T}{2}\sum_r N_J(r) q_G(\gamma_J(r)) + \frac{T}{2}\sum_i q_G(\gamma_Z(i)) +$$
$$\frac{T}{2}\sum_s N(s) q_G(\gamma_\sigma(s)) + \frac{T}{2}(I + M) - \frac{NT}{2}\log(2\pi)$$

where $$q_G(\gamma) = \psi(\gamma) - \log\gamma$$

As described above, the second learning data acquiring unit 113 repeats estimation of the current distribution expressed by Expression 5 and estimation of the current variance expressed by Expression 7 until the free energy in Expression 9 converges, and thereby acquires the second learning data.

Also, the second learning data acquiring unit 113 acquires the second learning data from the first learning data by using an electric field analysis technique and a technique for solving inverse problem that involves calculation using Expression 1 to Expression 9. Note that "electric field analysis" corresponds to analyzing interaction between a target object and an electromagnetic field by solving Maxwell's equations. The electric field analysis also includes static analysis, quasi-static analysis, dynamic analysis and the like.

The second learning data acquiring unit 113 can be generally realized by an MPU, memory or the like. The processing procedure of the second learning data acquiring unit 113 is generally realized by software, and the software for this is recorded in a recording medium such as a ROM. Note that the processing procedure also may be realized by hardware (dedicated circuitry).

The learning feature amount group acquiring unit 114 acquires a learning feature amount group including one or more feature amounts from the second learning data. The learning feature amount group acquiring unit 114 performs signal processing on the second learning data, and thereby acquires the learning feature amount group including one or more feature amounts. Here, "signal processing" refers to, for example, bias correction, baseline correction, detrending, mean value calculation, processing using a high-pass filter, processing using a low-pass filter, processing using FFT, processing using PCA, processing using ICA, calculation of phase locking value, calculation of moving average, sensor selection, time selection, reference correction, downsampling, upsampling, power calculation, envelop calculation (Hilbert transformation), processing using a spatial filter, processing using an inverse problem filter, and the like. "Feature amount" is data calculated by the signal processing described above, for example, and refers to a mean value, variance, phase locking value and the like. Note that a feature amount constituting the learning feature amount group may be any data as long as it indicates a feature of learning data. Also, the learning feature amount group acquiring unit 114 may perform plural types of signal processing. Also, since various types of signal processing given above as examples are known techniques, specific descriptions thereof are omitted.

The learning feature amount group acquiring unit 114 can be generally realized by an MPU, memory or the like. The processing procedure of the learning feature amount group acquiring unit 114 is generally realized by software, and the software for this is recorded in a recording medium such as a ROM. Note that the processing procedure also may be realized by hardware (dedicated circuitry).

The intention determination information accumulating unit 115 accumulates, in the intention determination information storage unit 111, intention determination information that includes a second learning feature amount group acquired by the learning feature amount group acquiring unit 114 and an intention identifier that identifies one intention.

The intention determination information accumulating unit 115 can be generally realized by an MPU, memory or the like. The processing procedure of the intention determination information accumulating unit 115 is generally realized by software, and the software for this is recorded in a recording medium such as a ROM. Note that the processing procedure also may be realized by hardware (dedicated circuitry).

The first brain activity data acquiring unit 116 acquires the first brain activity data, which is data of a brain activity, from the outside of the cranium of a user. The first brain activity data acquiring unit 116 generally has the same configuration as that of the first learning data acquiring unit 112. The first brain activity data acquiring unit 116 generally is a brain wave measuring apparatus.

The second brain activity data acquiring unit 117 converts the first brain activity data acquired from the outside of the cranium of a user to intracerebral brain activity data, and thereby acquires the second brain activity data. The second brain activity data acquiring unit 117 acquires the second brain activity data by applying the hierarchical variational Bayes approach to the first brain activity data.

More specifically, for example, the second brain activity data acquiring unit 117 converts the first brain activity data using Expression 1 and Expression 2 indicated above, and thereby acquires the second brain activity data. The second brain activity data acquiring unit 117 generally has the same configuration as that of the second learning data acquiring unit 113.

The second brain activity data acquiring unit 117 can be generally realized by an MPU, memory or the like. The processing procedure of the second brain activity data acquiring unit 117 is generally realized by software, and the software for this is recorded in a recording medium such as a ROM. Note that the processing procedure also may be realized by hardware (dedicated circuitry).

The feature amount group acquiring unit 118 performs signal processing on the second brain activity data, and thereby acquires an input feature amount group including one or more feature amounts. Here, "signal processing" refers to, for example, bias correction, baseline correction, detrending, mean value calculation, processing using a high-pass filter, processing using a low-pass filter, processing using FFT, processing using PCA, processing using ICA, calculation of phase locking value, calculation of moving average, sensor selection, time selection, reference correction, downsampling, upsampling, power calculation, envelop calculation (Hilbert transformation), processing using a spatial filter, processing using an inverse problem filter, and the like. "Feature amount" is data calculated by the signal processing described above, for example, and refers to a mean value, variance, phase locking value and the like, for example Note that a feature amount constituting the input feature amount group may be any data as long as it indicates a feature of brain activity data. Also, the feature amount group acquiring unit 118 may perform plural types of signal processing. Also, since various types of signal processing given above as examples are known techniques, specific descriptions thereof are omitted. The feature amount group acquiring unit 118 generally has the same configuration as that of the learning feature amount group acquiring unit 114.

The feature amount group acquiring unit 118 can be generally realized by an MPU, memory or the like. The processing procedure of the feature amount group acquiring unit 118 is generally realized by software, and the software for this is recorded in a recording medium such as a ROM. Note that the processing procedure also may be realized by hardware (dedicated circuitry).

The intention identifier acquiring unit 119 acquires the intention identifier that corresponds to the input feature amount group based on two or more pieces of intention determination information stored in the intention determination information storage unit 111. There is no restriction to the algorithm used for the intention identifier acquiring unit 119 to acquire the intention identifier. The intention identifier acquiring unit 119 calculates, for each intention identifier, a distance between the input feature amount group and the learning feature amount group included in the intention determination information, for example. Then, the intention identifier acquiring unit 119 may acquire an intention identifier that corresponds to the learning feature amount group having the smallest distance. The intention identifier acquiring unit 119 can be generally realized by an MPU, memory or the like. The processing procedure of the intention identifier acquiring unit 119 is generally realized by software, and the software for this is recorded in a recording medium such as a ROM. Note that the processing procedure also may be realized by hardware (dedicated circuitry).

The probability calculation section 1191 calculates the possibility that the input feature amount group acquired by the feature amount group acquiring unit 118 corresponds to each of two or more intention identifiers included in the two or more pieces of intention determination information, for each of the two or more intention identifiers, by using two or more pieces of intention determination information in the intention determination information storage unit 111.

In the case where there are two (two types of) intention identifiers, for example, the probability calculation section 1191 calculates the probability for each intention identifier as described below. Specifically, the probability calculation section 1191 obtains information on a boundary for classification into two classes (class 1 [first intention identifier] and class 2 [second intention identifier]), from the second learning feature amount group (vector). The concept of this is shown in FIG. 3.

Next, the probability calculation section 1191 calculates the distance between the boundary and the input feature amount group (see FIG. 4). Then, the probability calculation section 1191 applies the distance to a logistic function (sigmoid function), thereby converting the distance to a value from 0 to 1 (a value that is not less than 0 and not more than 1). Then, the probability calculation section 1191 obtains the converted value (0 to 1) as the probability of the first intention identifier. The probability calculation section 1191 calculates the probability of the second intention identifier by subtracting the probability of the first intention identifier from 1 (1−probability of first intention identifier).

Also, in the case where there are four (four types of) intention identifiers, for example, the probability calculation section 1191 calculates the probability for each intention identifier as described below. Specifically, the processing performed in the case of two intention identifiers is expanded. First, considering that there are two classes, namely, the first intention identifier and another intention identifier, the probability calculation section 1191 obtains information on a boundary for classification into two classes (class 1 [first intention identifier], and class 2 [first intention identifier, third intention identifier or fourth intention identifier]), from the second learning feature amount group (vector). Next, the probability calculation section 1191 calculates a distance between the boundary to the input feature amount group. Then, the probability calculation section 1191 applies the distance to a logistic function (sigmoid function), thereby converting the distance to a value from 0 to 1 (a value that is not less than 0 and not more than 1). Then, the probability calculation section 1191 obtains the converted value (0 to 1) as the probability of the first intention identifier. Next, the probability calculation section 1191 calculates the distance of a second learning feature amount group (vector) that corresponds to the second intention identifier, the third intention identifier or the fourth intention identifier by subtracting the probability of the first intention identifier from 1 (1−probability of first intention identifier).

Next, considering that there are two classes, namely, the second intention identifier and another intention identifier, the probability calculation section 1191 obtains information on a boundary for classification into two classes (class 1 [second intention identifier], and class 2 [first intention identifier, third intention identifier or fourth intention identifier]), from the second learning feature amount group (vector). Next, the probability calculation section 1191 calculates a distance between the boundary to the input feature amount group. Then, the probability calculation section 1191 applies the distance to a logistic function (sigmoid function), thereby converting the distance to a value from 0 to 1 (a value that is not less than 0 and not more than 1). Then, the probability calculation section 1191 obtains the converted value (0 to 1) as the probability of the second intention identifier. Next, the probability calculation section 1191 calculates the distance of the second learning feature amount group (vector) that corresponds to the first intention identifier, the third intention identifier or the fourth intention identifier by subtracting the probability of the second intention identifier from 1 (1−probability of second intention identifier).

Next, considering that there are two classes, namely, the third intention identifier and another intention identifier, the probability calculation section 1191 obtains information on a boundary for classification into two classes (class 1 [third intention identifier], and class 2 [first intention identifier, second intention identifier or fourth intention identifier]), from the second learning feature amount group (vector). Next, the probability calculation section 1191 calculates a distance between the boundary to the input feature amount group. Then, the probability calculation section 1191 applies the distance to a logistic function (sigmoid function), thereby converting the distance to a value from 0 to 1 (a value that is not less than 0 and not more than 1). Then, the probability calculation section 1191 obtains the converted value (0 to 1) as the probability of the third intention identifier. Next, the probability calculation section 1191 calculates the distance of the second learning feature amount group (vector) that corresponds to the first intention identifier, the second intention identifier or the fourth intention identifier by subtracting the probability of the third intention identifier from 1 (1−probability of third intention identifier).

Next, considering that there are two classes, namely, the fourth intention identifier and another intention identifier, the probability calculation section 1191 obtains information on a boundary for classification into two classes (class 1 [fourth intention identifier], and class 2 [first intention identifier, second intention identifier or third intention identifier]), from the second learning feature amount group (vector). Next, the probability calculation section 1191 calculates a distance between the boundary to the input feature amount group. Then, the probability calculation section 1191 applies the distance to a logistic function (sigmoid function), thereby converting the distance to a value from 0 to 1 (a value that is not less than 0 and no more than 1). Then, the probability calculation section 1191 obtains the converted value (0 to 1) as the probability of the fourth intention identifier. Next, the probability calculation section 1191 calculates the distance of the second learning feature amount group (vector) that corresponds to the first intention identifier, the second intention identifier or the third intention identifier by subtracting the probability of the fourth intention identifier from 1 (1−probability of fourth intention identifier).

Then, the probability calculation section 1191 acquires the probabilities of the first intention identifier to the fourth intention identifier by merging the probabilities acquired as described above. Here, "merge" refers to an operation for obtaining probabilities based on eight probabilities, namely, the probability (P1) of the first intention identifier, the probability (P234) of the intention identifiers other than the first intention identifier, the probability (P2) of the second intention identifier, the probability (P134) of the intention identifiers other than the second intention identifier, the probability (P3) of the third intention identifier, the probability (P124) of the intention identifiers other than the third intention identifier, the probability (P4) of the fourth intention identifier, and the probability (P123) of the intention identifiers other than the fourth intention identifier. It is preferable to obtain the merged probabilities of the first intention identifier, the second intention identifier, the third intention identifier and the fourth intention identifier respectively by the following expressions, "P1×P134×P124×P123", "P234×P2×P124×P123", "P234×P134×P3×P123", and "P234×P134×P124×P4". Note that an operation for normalizing the probabilities may be added. Here, "normalizing" refers to an operation in which each of the merged probabilities of the first intention identifier to the fourth intention identifier is divided by the total value thereof, such that the total of the probability values obtained by the division is 1.

The probability calculation section 1191 can be generally realized by an MPU, memory or the like. The processing procedure of the probability calculation section 1191 is generally realized by software, and the software for this is recorded in a recording medium such as a ROM. Note that the processing procedure also may be realized by hardware (dedicated circuitry).

The intention identifier acquiring section 1192 acquires an intention identifier that corresponds to the largest probability of the probabilities of the respective intention identifiers calculated by the probability calculation section 1191.

The intention identifier acquiring section 1192 can be generally realized by an MPU, memory or the like. The processing procedure of the intention identifier acquiring section 1192 is generally realized by software, and the software for this is recorded in a recording medium such as a ROM. Note that the processing procedure also may be realized by hardware (dedicated circuitry).

The intention identifier output unit 120 outputs an intention identifier acquired by the intention identifier acquiring unit 119. Here, "output" may preferably be output to the robot 12, but may be output to a display, sound output, and the like. The intention identifier output unit 120 can be realized, for example, by a communication means for sending an intention identifier to the robot 12.

The operation information storage unit 121 can have two or more pieces of operation information stored therein. The operation information refers to a set of an intention identifier and an operation module that causes the operation corresponding to the intention identifier to be performed. The operation module may be realized by either of hardware or software, or both. Although the operation information storage unit 121 preferably is a non-volatile recording medium, it can be also realized by a volatile recording medium. There is no restriction to the process by which the operation information is stored in the operation information storage unit 121. For example, operation information may be stored in the operation information storage unit 121 via a recording medium, or operation information sent via a communication line or the like may be stored in the operation information storage unit 121. Alternatively, operation information input via an input device may be stored in the operation information storage unit 121.

The intention identifier accepting unit 122 accepts an intention identifier output from the brain information output apparatus 11. "Accept" means receiving by a communication means, delivery of information (intention identifier) by software, and the like.

The execution unit 123 executes the operation module corresponding to the intention identifier accepted by the intention identifier accepting unit 122. The operation module may realize any operation. The execution unit 123 can be generally realized by an MPU, memory or the like. The processing procedure of the execution unit 123 is generally realized by software, and the software for this is recorded in a recording medium such as a ROM. Note that the processing procedure also may be realized by hardware (dedicated circuitry).

Next, the operation of the robot system 1 will be described. First, the operation of the brain information output apparatus 11 will be described. FIG. 5 is a flowchart illustrating the operation in which the brain information output apparatus 11 acquires learning data. Here, the learning data refers to the intention determination information.

(Step S501) The first learning data acquiring unit 112 determines whether or not to acquire first learning data. If the first learning data is to be acquired, the procedure proceeds to step S502, and if not, the procedure proceeds to step S504. Note that in order to acquire the first learning data, for example, an output means, not shown in the drawings, outputs to a user an instruction that indicates performance of an operation corresponding to an intention (including thinking, imagining and the like). After such an instruction is output, the first learning data acquiring unit 112 determines that the first learning data is to be acquired for a predetermined period (for example, 10 seconds). Also, "instruction that indicates performance of an operation corresponding to an intention" refers to information of a message, for example, "Please wave your right hand for 10 seconds", or "Please flutter your feet for 15 seconds".

(Step S502) The first learning data acquiring unit 112 acquires first learning data from the outside of the cranium of the user.

(Step S503) The first learning data acquiring unit 112 accumulates, at least temporarily, the first learning data acquired in step S502 in a recording medium. Note that the first learning data acquiring unit 112 generally accumulates first learning data in association with an intention identifier for identifying an intention, as a pair. Then, the procedures returns to step S501.

(Step S504) The first learning data acquiring unit 112 determines whether or not to end the processing for acquiring first learning data. If the processing is to be ended, the procedure proceeds to step S505, and if not, the procedure returns to step S501. Note that the first learning data acquiring unit 112 determines to end the processing for acquiring first learning data in the case where first learning data sets corresponding to all intention identifiers has been acquired, for example.

(Step S505) The second learning data acquiring unit 113 performs conversion processing on all of the acquired first learning data sets, and thereby acquires second learning data. The conversion processing refers to processing for converting first learning data acquired from the outside of the cranium of the user to second learning data, which is data of an intracerebral brain activity. An example of the conversion processing will be described with reference to the flowchart in FIG. 6. Note that the second learning data acquiring unit 113 generally performs this conversion to second learning data for each set of first learning data (first learning data that is time-series data acquired by a single trial).

(Step S506) The second learning data acquiring unit 113 accumulates, at least temporarily, the second learning data acquired in step S505 in a recording medium. The second learning data acquiring unit 113 generally accumulates each set of second learning data in association with an intention identifier.

(Step S507) The learning feature amount group acquiring unit 114 acquires, from the second learning data accumulated in step S506, a learning feature amount group including one or more feature amounts. Here, the learning feature amount group acquiring unit 114 generally acquires a plurality of learning feature amount groups.

(Step S508) The intention determination information accumulating unit 115 configures intention determination information by the learning feature amount group acquired by the learning feature amount group acquiring unit 114 and an intention identifier for identifying one intention. Note that generally, an intention identifier is managed in association with the first learning data or the second learning data. Also, the intention determination information accumulating unit 115 generally configures a plurality of intention determination information sets.

(Step S509) The intention determination information accumulating unit 115 accumulates one or more intention determination information pieces configured in step S508 in the intention determination information storage unit 111, and ends the processing.

Next, the conversion processing performed in step S505 will be described with reference to the flowchart in FIG. 6.

(Step S601) The second learning data acquiring unit 113 performs the direct problem analysis using an electric field analysis technique, and calculates the lead field matrix G indicated in Expression 1.

(Step S602) The second learning data acquiring unit 113 calculates the hierarchical prior distribution of the current distribution J prior to observation of the electric field E, as indicated in Expression 4.

(Step S603) The second learning data acquiring unit 113 estimates the current distribution as indicated in Expression 5.

(Step S604) The second learning data acquiring unit 113 updates parameters as indicated in Expression 6.

(Step S605) The second learning data acquiring unit 113 estimates the current variance as indicated in Expression 7.

(Step S606) The second learning data acquiring unit 113 updates parameters as indicated in Expression 8.

(Step S607) The second learning data acquiring unit 113 calculates the free energy F as indicated in Expression 9.

(Step S608) The second learning data acquiring unit 113 determines whether a change in the calculated free energy is less than a predetermined threshold. If the change is less than the threshold, the procedure proceeds to step S609, and if the change is greater than the threshold, the procedure returns to step S603.

(Step S609) The second learning data acquiring unit 113 outputs the currently obtained J as second learning data, and ends the processing.

Next, the operation in which the brain information output apparatus 11 outputs an intention identifier will be described with reference to the flowchart in FIG. 7.

(Step S701) The first brain activity data acquiring unit 116 determines whether or not the first brain activity data has been acquired. If the first brain activity data has been acquired, the procedure proceeds to step S702, and if not, the procedure returns to step S701.

(Step S702) The second brain activity data acquiring unit 117 performs conversion processing on the first brain activity data acquired in step S701, and thereby acquires the second brain activity data. Note that the conversion processing was described with reference to the flowchart in FIG. 6.

(Step S703) The feature amount group acquiring unit 118 acquires an input feature amount group from the second brain activity data acquired in step S702.

(Step S704) The intention identifier acquiring unit 119 receives the input feature amount group acquired in step S703 as an input, and acquires an intention identifier corresponding to the input feature amount group. This intention identifier acquiring processing will be described with reference to the flowchart in FIG. 8.

(Step S705) The intention identifier output unit 120 outputs the intention identifier acquired in step S704 to the robot 12. Then, the procedure returns to step S701.

Note that in the flowchart in FIG. 7, the processing ends due to powering off or interruption for aborting the processing.

Next, an example of the intention identifier acquiring processing in step S704 will be described with reference to the flowchart in FIG. 8.

(Step S801) The intention identifier acquiring unit 119 sets a counter i to 1.

(Step S802) The intention identifier acquiring unit 119 determines whether or not an i-th intention identifier exists. If the i-th intention identifier exists, the procedure proceeds to step S803, and if not, the procedure proceeds to step S808.

(Step S803) The intention identifier acquiring unit 119 acquires a learning feature amount group (vector) corresponding to the i-th intention identifier.

(Step S804) The intention identifier acquiring unit 119 acquires a feature amount group (vector) that has been input.

(Step 805) The intention identifier acquiring unit 119 calculates the distance between the learning feature amount group (vector) acquired in step S803 and the feature amount group (vector) acquired in step S804.

(Step S806) The intention identifier acquiring unit 119 accumulates, at least temporarily, the distance acquired in step S805 and the i-th intention identifier associated with each other in a recording medium.

(Step S807) The intention identifier acquiring unit 119 then increments the counter i by 1, and the procedure returns to step S802.

(Step S808) The intention identifier acquiring unit 119 acquires an intention identifier using the distances accumulated in step S806. For example, the intention identifier acquiring unit 119 acquires an intention identifier paired with the smallest distance. Also, as described above, the intention identifier acquiring unit 119 may calculate the probability of each intention identifier, and acquire the intention identifier having the largest probability. Then, the procedure returns to superordinate processing.

Note that in the flowchart in FIG. 8, the operation in step S804 may be configured to be performed outside the loop, and may be performed only once.

Next, the operation by the robot 12 will be described with reference to the flowchart in FIG. 9.

(Step S901) The intention identifier accepting unit 122 determines whether or not the intention identifier output from the brain information output apparatus 11 has been accepted. If the intention identifier has been accepted, the procedure proceeds to step S902, and if not, the procedure returns to step S901.

(Step S902) The execution unit 123 reads out the operation module corresponding to the intention identifier accepted in step S901 from the operation information storage unit 121.

(Step S903) The execution unit 123 executes the operation module read out in step S902. Then, the procedure returns to step S901.

With the processing described above, an operation corresponding to an action (including thinking) intended by the user is performed by the robot 12.

Note that in the flowchart in FIG. 9, the processing ends due to powering off or interruption for aborting the processing.

As described above, in the present embodiment, brain activity data acquired from the outside of the cranium is converted to intracerebral brain activity data and used, and thereby intention determination can be performed with high accuracy.

Note that in the present embodiment, specific examples such as experimental examples have not been described. Specific examples will be described in Embodiment 2.

Furthermore, the processing in the present embodiment may be realized by software. Such software may be distributed by downloading of software product or the like. In addition, such software may be recorded on a recording medium such as a CD-ROM and distributed. Note that this applies to other embodiments of the invention as well. Software that realizes an information processing apparatus of the present embodiment may be a program as described below. That is, this program allows storage in a storage medium of two or more pieces of intention determination information, each intention determination information including a pair of an intention identifier that is information for identifying an intention of a user, and a learning feature amount group including one or more feature amounts extracted from second learning data that is obtained by converting first learning data into intracerebral brain activity data, the first leaning data being data of a brain activity acquired from the outside of the cranium of a user when the user performs a trial, which is a series of actions, according to an intention identified by the intention identifier, and causes a computer to function as a first brain activity data acquiring unit that acquires first brain activity data, which is data of a brain activity, from the outside of the cranium of a user; a second brain activity data acquiring unit that converts the first brain activity data acquired from the outside of the cranium of a user to intracerebral brain activity data, and acquires second brain activity data; a feature amount group acquiring unit that acquires, from the second brain activity data, an input feature amount group including one or more feature amounts; an intention identifier acquiring unit that acquires an intention identifier corresponding to the input feature amount group based on the two or more pieces of intention determination information stored in the storage medium; and an intention identifier output unit that outputs the intention identifier acquired by the intention identifier acquiring unit.

Also, with the program, it is preferable that the computer is caused to function as a first learning data acquiring unit that acquires, when a user performs a trial, which is a series of actions, according to one intention, first learning data, which is time-series data indicating a brain activity, from the outside of the cranium of the user using one or more sensors, for each of the sensors; a second learning data acquiring unit that converts the first learning data acquired from the outside of the cranium of a user to data of an intracerebral brain activity, and acquires second learning data; a learning feature amount group acquiring unit that acquires, from the second learning data, a learning feature amount group including one or more feature amounts; and an intention determination information accumulation unit that accumulates, in the storage medium, intention determination information including the second learning feature amount group and an intention identifier for identifying the one intention.

Also, with the program, it is preferable that the computer is caused to function such that the second brain activity data acquiring unit acquires second brain activity data by applying the hierarchical variational Bayes approach to the first brain activity data.

Also, with the program, it is preferable that the computer is caused to function such that the intention identifier acquiring unit includes: a probability calculation section that calculates a probability that the input feature amount group acquired by the feature amount group acquiring unit corresponds to each of two or more intention identifiers included in the two or more pieces of intention determination information in the intention determination information storage unit, using the two or more pieces of intention determination information, for each of the two or more intention identifiers; and an intention identifier acquiring section that acquires an intention identifier that corresponds to a largest probability based on the probabilities of the intention identifiers calculated by the probability calculation section.

Embodiment 2

In the present embodiment, a brain information output apparatus will be described that converts first brain activity data acquired from the outside of the cranium to second brain activity data (intracerebral brain activity data), and detects an intention by using the second brain activity data.

In particular, in the present embodiment, a brain information output apparatus will be described that determines an intention of a user based on a plurality of brain activity data sets obtained by a plurality of brain activity measurement devices.

Also, in the present embodiment, a brain information output apparatus will be described that includes one or more sensors, and that, in the case where a plurality of learning data sets are acquired by a plurality of trials, removes inappropriate learning data sets and detects an intention using appropriate learning data sets only.

The conceptual diagram of a robot system 2 according to the present embodiment is the same as FIG. 1. The robot system 2 includes a brain information output apparatus 21 and a robot 12. FIG. 10 is a block diagram of the robot system 2 of the present embodiment. The brain information output apparatus 21 constituting the robot system 2 includes an intention determination information storage unit 1011, a first learning data acquiring unit 1012, an abnormal data removing unit 1011, a second learning data acquiring unit 1013, a learning feature amount group acquiring unit 1014, an intention determination information accumulation unit 1015, a first brain activity data acquiring unit 1016, a second brain activity data acquiring unit 1017, a feature amount group acquiring unit 1018, an intention identifier acquiring unit 1019, and an intention identifier output unit 120.

The abnormal data removing unit 1011 includes an abnormal trial removing section 10111 and an abnormal sensor removing section 10112.

The intention identifier acquiring unit 1019 includes a probability calculation section 10191 and an intention identifier acquiring section 10192.

Two or more types of intention determination information may be stored in the intention determination information storage unit 1011. Two or more types of intention determination information include two or more types of learning feature amount groups (normal learning feature amount groups to be described below) that have been acquired from two or more types of first learning data. The intention determination information refers to information in which an intention identifier and a learning feature amount group are paired. Although the intention determination information storage unit 1011 preferably is a non-volatile recording medium, it can be also realized by a volatile recording medium. Note that the two or more types of learning data refers to, for example, NIRS data and brain wave data.

The first learning data acquiring unit 1012 acquires two or more types of first learning data from the outside of the cranium of the user. "Two types" refers to two different types of brain activity data, for example, NIRS data and brain wave data. Also, the first learning data acquiring unit 1012 may acquire three or more types of brain activity data. The first learning data acquiring unit 1012 is configured by, for example, a near-infrared spectroscopy apparatus (NIRS apparatus) and a brain wave measuring apparatus. The NIRS apparatus is an apparatus that applies the principal of light functional imaging in which functional brain mapping is non-invasively performed on the scalp using near-infrared light. Also, the brain wave measuring apparatus is for measuring brain waves. As a device that includes a function of measuring brain waves, an apparatus manufactured by BioSemi (called "ActiveTwo System") can be given as an example. Also, the first learning data acquiring unit 1012 may include a functional MRI (fMRI: functional Magnetic Resonance Imaging) or PET (Positron Emission Tomography) apparatus, for example.

The abnormal data removing unit 1011 acquires one or more partial learning data sets from the first learning data, acquires a feature value for each of the partial learning data sets, and determines whether the partial learning data is normal or abnormal using the feature values. The abnormal data removing unit 1011 removes partial learning data determined to be abnormal from the learning data, and thereby acquires normal learning data. The feature value may be the value of the partial learning data or may be a mean value or a standard deviation. Note that the normal learning data corresponds to data acquired from the outside of the cranium as is. The abnormal data removing unit 1011 acquires normal learning data from each of the two or more types of first learning data. That is, the abnormal data removing unit 1011 acquires two or more types of normal learning data.

Also, the feature value refers to the number of sensor data sets that have been determined to have a deviation of a predetermined level or larger, by using, for example, either a mean value and the standard deviation of all data sets constituting the learning data, or a mean value and the standard deviation of the differential values of all data sets constituting the learning data, or both.

Also, the feature value refers to the number of trials that have been determined to have a deviation of a predetermined level or larger, by using, for example, either a mean value and the standard deviation of all data sets constituting the learning data, or a mean value and the standard deviation of the differential values of all data sets constituting the learning data, or both.

Also, the abnormal data removing unit 1011 preferably includes both the abnormal trial removing section 10111 and the abnormal sensor removing section 10112 to be described below, but may include one of them. Also, the abnormal data removing unit 1011 may, instead of including both the abnormal trial removing section 10111 and the abnormal sensor removing section 10112, examine each data constituting the learning data, and individually remove data that has been determined to have a deviation of a predetermined level or larger, by using, for example, either a mean value and the standard deviation of all data sets constituting the learning data, or a mean value and the standard deviation of the differential values of all data sets constituting the learning data, or both.

The abnormal data removing unit 1011 can be generally realized by an MPU, memory or the like. The processing procedure of the abnormal data removing unit 1011 is generally realized by software, and the software for this is recorded in a recording medium such as a ROM. Note that the processing procedure also may be realized by hardware (dedicated circuitry).

The abnormal trial removing section 10111 acquires the feature value of partial learning data of each trial, and determines whether partial learning data is normal or abnormal using the corresponding feature value. The abnormal trial removing section 10111 removes partial learning data determined to be abnormal (all data constituting the trial corresponding to the removed partial learning data) from the learning data, and thereby acquires normal learning data. Note that here, there may be a case in which inappropriate data is additionally removed from the acquired acquire normal learning data, thereby acquiring final normal learning data.

It is preferable that if the abnormal trial removing section 10111 has determined that a certain partial learning data set has a deviation of a predetermined level or larger relative to other partial learning data sets based on the feature values of the partial learning data sets of the respective trials, it removes that partial learning data set from the learning data, and thereby acquires normal learning data.

More specifically, it is preferable that if the abnormal trial removing section 10111 has determined that, out of sensor data sets constituting certain partial learning data, at least a predetermined number of the sensor data sets have a deviation of a predetermined level or larger, it removes that partial learning data from the learning data, and thereby acquires normal learning data. Whether each sensor data set constituting partial learning data has a deviation of a predetermined level or larger is determined using either a mean value and the standard deviation of all data sets constituting the learning data, or a mean value and the standard deviation of the differential values of all data sets constituting the learning data, or both. Note that the partial learning data removed in the above description refers to the entire data of the trial determined to be abnormal.

The abnormal trial removing section 10111 can be generally realized by an MPU, memory or the like. The processing procedure of the abnormal trial removing section 10111 is generally realized by software, and the software for this is recorded in a recording medium such as a ROM. Note that the processing procedure also may be realized by hardware (dedicated circuitry).

The abnormal sensor removing section 10112 acquires the feature value of partial learning data of each sensor, and determines whether partial learning data is normal or abnormal using the corresponding feature value. The abnormal sensor removing section 10112 removes partial learning data determined to be abnormal from learning data, and thereby acquires normal learning data.

If the abnormal sensor removing section 10112 has determined that a certain partial learning data set has a deviation of a predetermined level or larger relative to other partial learning data sets based on the feature values of the partial learning data sets of the respective sensors, it removes that partial learning data set from the learning data, and thereby acquires normal learning data.

More specifically, if the abnormal sensor removing section 10112 has determined that, out of trial data sets constituting certain partial learning data, at least a predetermined number of the trial data sets have a deviation of a predetermined level or larger, it removes that partial learning data from the learning data, and thereby acquires normal learning data. Whether each trial data constituting partial learning data has a deviation of a predetermined level or larger is determined using either a mean value and the standard deviation of all data sets constituting the learning data, or a mean value and the standard deviation of the differential values of all data sets constituting the learning data, or both. Note that the partial learning data removed in the above description refers to the entire data of the sensor determined to be abnormal.

The abnormal sensor removing section 10112 can be generally realized by an MPU, memory or the like. The processing procedure of the abnormal sensor removing section 10112 is generally realized by software, and the software for this is recorded in a recording medium such as a ROM. Note that the processing procedure also may be realized by hardware (dedicated circuitry).

The second learning data acquiring unit 1013 converts normal learning data, which is obtained by the abnormal data removing unit 1011 removing data from the data acquired from the outside of the cranium of the user, to the data of an intracerebral brain activity, and thereby acquires the second learning data. The second learning data acquiring unit 1013 may convert two or more types of normal learning data to two types of second learning data. The second learning data acquiring unit 1013 applies the hierarchical variational Bayes approach to two or more types of normal learning data, and thereby acquires two or more types of second learning data. The processing performed by the second learning data acquiring unit 1013 for acquiring second learning data from a single set of normal learning data is the same as that performed by the second learning data acquiring unit 113.

The second learning data acquiring unit 1013 can be generally realized by an MPU, memory or the like. The processing procedure of the second learning data acquiring unit 1013 is generally realized by software, and the software for this is recorded in a recording medium such as a ROM. Note that the processing procedure also may be realized by hardware (dedicated circuitry).

The learning feature amount group acquiring unit 1014 acquires two or more types of learning feature amount groups, each learning feature amount group including one or more feature amounts, from each of the two or more types of second learning data acquired by the second learning data acquiring unit 1013. The learning feature amount group acquiring unit 1014 performs signal processing on the second learning data, and thereby acquires a learning feature amount group including one or more feature amounts. Here, "signal processing" refers to, for example, bias correction, baseline correction, detrending, mean value calculation, processing using a high-pass filter, processing using a low-pass filter, processing using FFT, processing using PCA, processing using ICA, calculation of phase locking value, calculation of moving average, sensor selection, time selection, reference correction, downsampling, upsampling, power calculation, envelop calculation (Hilbert transformation), processing using a spatial filter, processing using an inverse problem filter, and the like. "Feature amount" is data calculated by the signal processing described above, for example, and refers to a mean value, variance, phase locking value and the like. Note that a feature amount constituting the learning feature amount group may be any data as long as it indicates a feature of the second learning data. Also, the learning feature amount group acquiring unit 1014 may perform two or more types of signal processing. Also, since various types of signal processing given above as examples are known techniques, specific descriptions thereof are omitted.

The learning feature amount group acquiring unit 1014 can be generally realized by an MPU, memory or the like. The processing procedure of the learning feature amount group acquiring unit 1014 is generally realized by software, and the software for this is recorded in a recording medium such as a ROM. Note that the processing procedure also may be realized by hardware (dedicated circuitry).

The intention determination information accumulation unit 1015 accumulates, in the intention determination information storage unit 1011, intention determination information including a normal learning feature amount group and an intention identifier for identifying one intention. The intention determination information accumulation unit 1015 generally accumulates, at least, intention determination information corresponding to all intention identifiers in the intention determination information storage unit 1011. The intention determination information accumulation unit 1015 accumulates two or more types of intention determination information in the intention determination information storage unit 1011.

The intention determination information accumulation unit 1015 can be generally realized by an MPU, memory or the like. The processing procedure of the intention determination information accumulation unit 1015 is generally realized by software, and the software for this is recorded in a recording medium such as a ROM. Note that the processing procedure also may be realized by hardware (dedicated circuitry).

The first brain activity data acquiring unit 1016 acquires two or more types of first brain activity data from the outside of the cranium of the user. The first brain activity data refers to two or more types of data from among data acquired by, for example, NIRS (near-infrared spectrophotometry), fMRI (functional Magnetic Resonance Imaging), MEG (magnetoencephalograph), or EEG (electroencephalograph). The first brain activity data and the normal learning data are the same type of data.

The first brain activity data acquiring unit 1016 is configured by, for example, an NIRS apparatus and a brain wave measuring apparatus. Also, the first brain activity data acquiring unit 1016 may include an fMRI or PET (Positron Emission Tomography) apparatus, for example. The first brain activity data acquiring unit 1016 is generally the same as the first learning data acquiring unit 1012.

The second brain activity data acquiring unit 1017 converts each of two or more types of first brain activity data acquired from the outside of the cranium of the user to intracerebral brain activity data, and thereby acquires two or more types of second brain activity data.

More specifically, for example, the second brain activity data acquiring unit 117 converts each of two or more types of first brain activity data using the-above-indicated Expression 1 and Expression 2, and thereby obtains two or more types of second brain activity data.

The second brain activity data acquiring unit 1017 can be generally realized by an MPU, memory or the like. The processing procedure of the second brain activity data acquiring unit 1017 is generally realized by software, and the software for this is recorded in a recording medium such as a ROM. Note that the processing procedure also may be realized by hardware (dedicated circuitry).

The feature amount group acquiring unit 1018 performs signal processing on each of the two or more types of second brain activity data, and thereby acquires input feature amount groups, each input feature amount group including one or more feature amounts. Here, two or more types of input feature amount groups are acquired. The method of the signal processing is as described above.

The feature amount group acquiring unit 1018 can be generally realized by an MPU, memory or the like. The processing procedure of the feature amount group acquiring unit 1018 is generally realized by software, and the software for this is recorded in a recording medium such as a ROM. Note that the processing procedure also may be realized by hardware (dedicated circuitry).

The intention identifier acquiring unit 1019 acquires an intention identifier corresponding to an input feature amount group based on two or more pieces of intention determination information stored in the intention determination information storage unit 1011. There is no restriction to the algorithm used for the intention identifier acquiring unit 1019 to acquire the intention identifier. For example, the intention identifier acquiring unit 1019 calculates, for each intention identifier, the distance between the input feature amount group and the learning feature amount group included in the intention determination information. Then, the intention identifier acquiring unit 1019 may acquire an intention identifier that corresponds to the learning feature amount group having a smallest distance. Also, it is preferable that the intention identifier acquiring unit 1019 acquires an intention identifier using a machine learning algorithm, using two or more pieces of intention determination information as learning data, and input feature amount groups as input data. The intention identifier acquiring unit 1019 is a discriminator using a technique called sparse logistic regression, for example. The sparse logistic regression is a known technique disclosed at the URL, https://www.autonlab.org/autonweb/10400.html. Also, there is no restriction to the machine learning algorithm. The intention identifier acquiring unit 1019 may be a machine learning device using a technique such as SVM (in the case of 2-class discrimination), SVR, a decision tree, or the like. There is no restriction to the algorithm used for acquiring an intention identifier used in the intention identifier acquiring unit 1019.

It is preferable that the intention identifier acquiring unit 1019 acquires an intention identifier using each of two or more types of second brain activity data. It is preferable that the intention identifier acquiring unit 1019 acquires an intention identifier using the probability calculation section 10191 and the intention identifier acquiring section 10192.

The intention identifier acquiring unit 1019 can be generally realized by an MPU, memory or the like. The processing procedure of the intention identifier acquiring unit 1019 is generally realized by software, and the software for this is recorded in a recording medium such as a ROM. Note that the processing procedure also may be realized by hardware (dedicated circuitry).

The probability calculation section 10191 calculates, for each type of the learning feature amount groups included in the intention determination information, and for each intention identifier, the probability of the corresponding input feature amount group. For example, a case is considered in which the first brain activity data acquiring unit 1016 is configured by an NIRS apparatus and a brain wave measuring apparatus. Also, it is assumed that four types of intention identifiers, "Left" indicating the left hand, "Right" indicating the right hand, "Tongue" and "Foot", are used.

In this case, the probability calculation section 10191 acquires eight probabilities, namely, probability ($P^{NIRS}_{Left}$), which is acquired from NIRS data and corresponds to the intention identifier "Left", probability ($P^{NIRS}_{Right}$), which is acquired from NIRS data and corresponds to the intention identifier "Right", probability ($P^{NIRS}_{Tongue}$), which is acquired from NIRS data and corresponds to the intention identifier "Tongue", probability ($P^{NIRS}_{Foot}$), which is acquired from NIRS data and corresponds to the intention identifier "Foot", probability ($P^{EEG}_{Left}$), which is acquired from brain wave data and corresponds to the intention identifier "Left", probability ($P^{EEG}_{Right}$), which is acquired from brain wave data and corresponds to the intention identifier "Right", probability ($P^{EEG}_{Tongue}$), which is acquired from brain wave data and corresponds to the intention identifier "Tongue", and probability ($P^{EEG}_{Foot}$), which is acquired from brain wave data and corresponds to the intention identifier "Foot". The method used by the probability calculation section 10191 for calculating the probabilities is the same as that used by the probability calculation section 1191, for example.

Then, next, the probability calculation section 10191 integrates the eight probabilities indicated above (probabilities for each intention identifier acquired based on two types of data) by using Expression 10, and thereby calculates an ultimate probability for each intention identifier. $P^{total}_{text}$ represents the ultimate probability. $P^{total}_{text}$ is an ultimate probability of an intention identifier TEXT (Left, Right, Tongue or Foot). Note that the probability calculation section 10191 retains information of Expression 10 in advance.

[Expression 10]
$$\begin{pmatrix} P^{total}_{Left} \\ P^{total}_{Right} \\ P^{total}_{Tongue} \\ P^{total}_{Foot} \end{pmatrix} = \begin{pmatrix} P^{EEG}_{Left} \times [P^{NIRS}_{Left}]^W \\ P^{EEG}_{Right} \times [P^{NIRS}_{Right}]^W \\ P^{EEG}_{Tongue} \times [P^{NIRS}_{Tongue}]^W \\ P^{EEG}_{Foot} \times [P^{NIRS}_{Foot}]^W \end{pmatrix} \bigg/ \left( \sum_i P^{EEG}_i \times (P^{NIRS}_i)^W \right)$$

Note that in Expression 10, "w" is a weight parameter indicating weight. When w=1, it is indicated that a first probability (probability acquired from brain wave data) and a second probability (probability acquired from NIRS data) are handled with an equal weight. When w=2, it is indicated that the second probability is treated with a larger weight than the first probability.

Also, in Expression 10, "i" is one of the intention identifiers "Left, Right, Tongue and Foot". Furthermore, $P^{NIRS}_i$ is a probability obtained from an NIRS apparatus (NIRS data), and $P^{EEG}_i$ is a probability obtained from a brain wave measuring apparatus (brain wave data).

Also, the probability calculation section 10191 may acquire an ultimate probability of each intention identifier, by using, for each type of the brain activity data (for example, each of NIRS data, brain wave data and the like), only intentions suitable for the corresponding data type (for example, "Left" indicating left hand and "Right" indicating right hand for NIRS data, and "Tongue" and "Foot" for brain wave data). In this case, the probability calculation section 10191 holds information for identifying the type of brain activity data in association with an intention identifier for identifying the intention suitable for that type of the brain activity data.

The probability calculation section 10191 can be generally realized by an MPU, memory or the like. The processing procedure of the probability calculation section 10191 is generally realized by software, and the software for this is recorded in a recording medium such as a ROM. Note that the processing procedure also may be realized by hardware (dedicated circuitry).

The intention identifier acquiring section 10192 acquires an intention identifier that corresponds to the largest probability of the ultimate probabilities obtained for each intention identifier. The intention identifier acquiring section 10192 generally acquires only one intention identifier. The intention identifier acquiring section 10192 can be generally realized by an MPU, memory or the like. The processing procedure of the intention identifier acquiring section 10192 is generally realized by software, and the software for this is recorded in a recording medium such as a ROM. Note that the processing procedure also may be realized by hardware (dedicated circuitry).

Next, the operation of the robot system 2 will be described. First, the operation of the brain information output apparatus 21 will be described. FIG. 11 shows a flowchart for illustrating an operation in which the brain information output apparatus 21 acquires learning data. Here, the learning data refers to intention determination information. Note that FIG. 11 shows a flowchart that can support three or more types of learning data.

(Step S1101) The first learning data acquiring unit 1012 determines whether or not to acquire first learning data. If the first learning data is to be acquired, the procedure proceeds to step S1102, and if not, the procedure proceeds to step S1104. Note that in order to acquire the first learning data, for example, an output section, not shown in the drawings, outputs to a user an instruction that indicates performance of an operation corresponding to an intention (including thinking, imagining and the like). After such an instruction is output, the first learning data acquiring unit 112 determines that the first learning data is to be acquired, for a predetermined period (for example, 10 seconds). Also, "instruction that indicates performance of an operation corresponding to an intention" refers to information of a message, for example, "Please wave your right hand for 10 seconds", or "Please flutter your feet for 15 seconds".

(Step S1102) The first learning data acquiring unit 1012 acquires first learning data of all types from the outside of the cranium of the user.

(Step S1103) The first learning data acquiring unit 1012 accumulates, at least temporarily, the first learning data of all types acquired in step S1102 in a recording medium. Note that the first learning data acquiring unit 1012 generally accumulates each of various types of first learning data in association with an intention identifier for identifying an intention, as a pair. Then, the procedures returns to step S1101.

(Step S1104) The first learning data acquiring unit 112 determines whether or not to end the processing for acquiring first learning data. If the processing is to be ended, the procedure proceeds to step S1105, and if not, the procedure returns to step S1101. Note that the first learning data acquiring unit 112 determines to end the processing for acquiring first learning data in the case where first learning data corresponding to all intention identifiers has been acquired, for example.

(Step S1105) The abnormal data removing unit 1011 assigns "1" to the counter i.

(Step S1106) The abnormal data removing unit 1011 determines whether or not first learning data of the i-th type exists. If first learning data of the i-th type exists, the procedure proceeds to step S1107, and if not, the procedure proceeds to superordinate processing.

(Step S1107) The abnormal data removing unit 1011 performs the abnormal data removing processing on the first learning data of the i-th type. Then, the abnormal data removing unit 1011 acquires normal learning data of the i-th type. The abnormal data removing processing will be described with reference to the flowchart in FIG. 12.

(Step S1108) The second learning data acquiring unit 1013 performs conversion processing on the normal learning data of the i-th type, and thereby acquires the second learning data. The conversion processing refers to processing for converting normal learning data acquired from the outside of the cranium of the user to the second learning data, which is data of an intracerebral brain activity. An example of the conversion processing was described with reference to the flowchart in FIG. 6.

(Step S1109) The second learning data acquiring unit 1013 accumulates, at least temporarily, the second learning data acquired in step S1108 in a recording medium.

(Step S1110) The learning feature amount group acquiring unit 1014 acquires, from the second learning data accumulated in step S1109, a learning feature amount group including one or more feature amounts.

(Step S1111) The intention determination information accumulation unit 1015 configures intention determination information by the learning feature amount group acquired by the learning feature amount group acquiring unit 1014 and an intention identifier for identifying one intention. Note that generally, an intention identifier is managed in association with the first learning data, the normal learning data, or the second learning data.

(Step S1112) The intention determination information accumulation unit 1015 accumulates the intention determination information configured in step S1108 in the intention determination information storage unit 1011, and ends the processing.

(Step S1113) The abnormal data removing unit 1011 increments the counter i by 1. Then, the procedure returns to step S1106.

Next, the abnormal data removing processing performed in step S1107 will be described with reference to the flowchart in FIG. 12.

(Step S1201) The abnormal data removing unit 1011 assigns "1" to the counter i.

(Step S1202) The abnormal data removing unit 1011 determines whether or not the i-th sensor exists. If the i-th sensor exists, the procedure proceeds to step S1203, and if not, the procedure proceeds to step S1210.

(Step S1203) The abnormal data removing unit 1011 acquires a mean value and the standard deviation of all data sets of all trials acquired by the i-th sensor. Note that in this case, it is preferable that the abnormal data removing unit 1011 sets the mean value of the entire time-series data of the i-th sensor as a reference point, and performs reference correction. Also, it is preferable that an absolute value of the amplitude is obtained from the corrected waveform for each sample, and the top x % (for example, x=5) of the samples in terms of largest value is regarded as falling outside of the confidence interval, and thus is discarded.

(Step S1204) The abnormal data removing unit 1011 assigns "1" to a counter j.

(Step S1205) The abnormal data removing unit 1011 determines whether or not the j-th trial exists. If the j-th trial exists, the procedure proceeds to step S1206, and if not, the procedure proceeds to step S1209.

(Step S1206) The abnormal data removing unit 1011 acquires all samples (entire data) of the j-th trial of the i-th sensor.

(Step S1207) The abnormal data removing unit 1011 determines whether each sample (data) acquired in step S1206 has a deviation of a predetermined level or larger. Then, the abnormal data removing unit 1011 registers samples that have a deviation of a predetermined level or larger as inappropriate data. Note that for example, the abnormal data removing unit 1011 obtains, for each sample, how many fold the absolute value is with respect to the standard deviation. Then, the abnormal data removing unit 1011 determines a sample whose absolute value is nine times of the standard deviation or larger to be inappropriate data.

(Step S1208) The abnormal data removing unit 1011 increments the counter j by 1. The procedure then returns to step S1205.

(Step S1209) The abnormal data removing unit 1011 increments the counter i by 1. The procedure then returns to step S1202.

(Step S1210) The abnormal sensor removing section 10112 assigns "1" to the counter i.

(Step S1211) The abnormal sensor removing section 10112 determines whether or not the i-th sensor exists. If the i-th sensor exists, the procedure proceeds to step S1211, and if not, the procedure proceeds to step S1216.

(Step S1212) The abnormal sensor removing section 10112 acquires the number of inappropriate data sets in the data sets acquired by the i-th sensor.

(Step S1213) The abnormal sensor removing section 10112 determines whether or not the number of inappropriate data sets calculated in step S1212 is more than or equal to a predetermined number (or ratio). If the number is more than or equal to the predetermined number, the procedure proceeds to step S1214, and if not, the procedure proceeds to step S1216.

(Step S1214) The abnormal sensor removing section 10112 determines the i-th sensor to be "Bad Sensor", and erases the data acquired by the i-th sensor.

(Step S1215) The abnormal sensor removing section 10112 increments the counter i by 1. Then, the procedure returns to step S1211.

(Step S1216) The abnormal trial removing section 10111 assigns "1" to the counter j.

(Step S1217) The abnormal trial removing section 10111 determines whether or not the j-th trial exists. If the j-th trial exists, the procedure proceeds to step S1218, and if not, the procedure returns to superordinate processing.

(Step S1218) The abnormal trial removing section 10111 acquires the number of inappropriate data sets in the data sets included in the j-th trial.

(Step S1219) The abnormal trial removing section 10111 determines whether or not the number of inappropriate data sets calculated in step S1218 is more than or equal to a predetermined number (or ratio). If the number is more than or equal to the predetermined number, the procedure proceeds to step S1220, and if not, the procedure proceeds to step S1221.

(Step S1220) The abnormal trial removing section 10111 determines the j-th trial to be "Bad Trial", and erases the data acquired by the j-th trial.

(Step S1221) The abnormal trial removing section 10111 increments the counter j by 1. Then, the procedure returns to step S1217.

Note that in the flowchart in FIG. 12, the algorithm used for removing data of abnormal trial and abnormal sensor is not limited to those described above.

Also, in the flowchart in FIG. 12, only abnormal trial data may be removed, or only abnormal sensor data may be removed.

Furthermore, in the flowchart in FIG. 12, removal of abnormal trial data and removal of abnormal sensor data may be performed in any order.

Next, the operation in which the brain information output apparatus 21 acquires an intention identifier using two or more pieces of intention determination information will be described with reference to the flowchart in FIG. 13.

(Step S1301) The first brain activity data acquiring unit 1016 determines whether or not first brain activity data has been acquired. If the brain activity data has been acquired, the procedure proceeds to step S1302, and if not, the procedure returns to step S1301.

(Step S1302) The first brain activity data acquiring unit 1016 accumulates, at least temporarily, the first brain activity data acquired in step S1301 in a recording medium.

(Step S1303) The first brain activity data acquiring unit 1016 determines whether or not brain activity data of all types has been acquired. If brain activity data of all types has been acquired, the procedure proceeds to step S1304, and if not, the procedure returns to step S1301. Note that the first brain activity data acquiring unit 1016 holds information for identifying all the types of brain activity data to be acquired (for example, "NIRS", "EEG" and the like).

(Step S1304) The second brain activity data acquiring unit 1017 assigns "1" to the counter i.

(Step S1305) The second brain activity data acquiring unit 1017 determines whether or not first brain activity data of the i-th type exists in the first brain activity data accumulated in step S1302. If the first brain activity data of the i-th type exists, the procedure proceeds to step S1306, and if not, the procedure proceeds to step S1310.

(Step S1306) The second brain activity data acquiring unit 1017 converts the first brain activity data of the i-th type and thereby obtains the second brain activity data of the i-th type. This conversion processing was described with reference to the flowchart in FIG. 6. Note that here, first brain activity data of all the types need not necessarily be subjected to the conversion processing, and first brain activity data of only one type (for example, brain wave data) may be subjected to the conversion processing.

(Step S1307) The feature amount group acquiring unit 1018 acquires an i-th feature amount group from the second brain activity data of the i-th type.

(Step S1308) The probability calculation section 10191 calculates an i-th probability for each intention identifier by using i-th intention determination information (that exists in the corresponding intention determination information storage unit).

(Step S1309) The second brain activity data acquiring unit 1017 increments the counter i by 1. Then, the procedure returns to step S1305.

(Step S1310) The probability calculation section 10191 calculates, for each intention identifier, an ultimate probability using the first probability to the (i−1)th probability. For example, Expression 10 can be used for this calculation.

(Step S1311) The intention identifier acquiring section 10192 acquires an intention identifier that corresponds to the largest probability of the ultimate probabilities calculated for the intention identifiers in step S1310.

(Step S1312) The intention identifier output unit 120 outputs the intention identifier acquired in step S1311. The processing is then ended.

A specific operation of the robot system 2 of the present embodiment will be described below. FIG. 1 shows a conceptual diagram of the robot system 2. This specific operation is described based on an experiment. Also, the operation of the robot system 1 is included in the operation of the robot system 2.

The brain information output apparatus 11 is an electronic device that functions as a so-called Brain Machine Interface (for actual motion of right and left hands). The intention identifier output from the brain information output apparatus 11 is sent to the robot 12, and the robot 12 performs an operation corresponding to the intention identifier.

Two adult males (Subject 1 and Subject 2) participated in this experiment. Subject 1 is familiar with the BMI. The other subject, Subject 2, has not experienced a full-scale BMI experiment. Each subject is requested to imagine motions related to the left hand (LEFT HAND), right hand (RIGHT HAND), tongue (TONGUE) and foot (FOOT), and brain waves and the cerebral blood flow change that occur during such imagining are measured simultaneously by an electroencephalograph and an NIRS measurement apparatus. In the experiment, estimation of the source of the current obtained by EEG is focused on, and analysis with respect to NIRS will not be performed. That is, with respect to NIRS data, the conversion processing by the second learning data acquiring unit 1013 and the second brain activity data acquiring unit 1017 is not performed. In addition, the first learning data acquiring unit 1012 and the first brain activity data acquiring unit 1016 are the electroencephalograph and the NIRS measurement apparatus, respectively. Furthermore, four intention identifiers, right hand, left hand, tongue and foot, are used.

Tasks performed by the subjects are described in FIG. 14.

The ActiveTwo system, which is a high-performance digital EEG manufactured by BioSemi, is used as the electroencephalograph, and measurement is performed through 64 channels at a sampling rate of 256 Hz. However, since precise measurement positions of the EEG are necessary for estimating current sources, the information on the positional relation between sensors and cerebral cortex was obtained, by overlaying structure images captured by FastSCAN manufactured by Polhemus and MRI for each experiment day.

In order to measure the cerebral blood flow change, FIORE-3000, which is an NIRS measurement apparatus and also is a brain functional imaging device for research use manufactured by Shimadzu Corporation, is used, and an amount of change in Oxy-Hb (oxygenated hemoglobin) is recorded at a sampling rate of 7.7 Hz using a 48-channel sensor placed centered on the vertex of the head.

Also, a simultaneous measurement cap manufactured by Shimadzu Corporation is used for simultaneously measuring brain waves and cerebral blood flow change.

Each subject sits facing a screen and the experiment is performed in a relaxed condition. Instructions are given through the screen and a speaker, and after a rest of ten seconds, a task instruction is given with a beep sound. The subject starts imagining two seconds after the instruction, and continues imagining for ten seconds at a constant rhythm. In order to give instructions, lattice points are presented during rest time, an arrow in the upward, downward, right or left direction is presented during task instruction, and a gazing point is presented during task. This flow of rest, task instruction and task is performed seven times for each task, namely, 28 times in total, which constitutes 1 run. Furthermore, 5 runs constitutes 1 Session, and the subject took a rest for half an hour between Sessions. Note that because of measurement preparation or the like, a rest for approximately one minute is also provided between runs. Trial data for 3 Sessions, which corresponds to 105 times of the flow for each task and 420 times of the flow in total, was measured in one day. The procedure of the experiment described thus far is as shown in FIG. 15.

Considering the theory of localization of brain function, it is expected that information including the active region may contribute to improvement of brain activity discrimination performance. Thus, in order to estimate the activity on the brain surface (intracerebral activity) based on the information measured on the scalp, the above-described hierarchical variational Bayes approach is applied so as to improve the brain activity discrimination performance. The hierarchical variational Bayes approach is as expressed in Expression 1 to Expression 9 mentioned above.

With respect to Expression 1, the number of sensors of the electroencephalograph (EEG) is in a range from 64 to approximately 128, at most. Specifically, the electric field E observed with Expression 1 involves approximately (64×1) vectors to (128×1) vectors. However, the number of points in the intracerebral current distribution is assumed to be several tens of thousands. That is, the intracerebral current J in Expression 1 involves approximately (several tens of thousands×1) vectors, and it is generally impossible to analytically solve Expression 1; this is called an ill-posed problem. In contrast, the current variance a is estimated after the current distribution J has been estimated using the hierarchical variational Bayes approach, and then the current distribution J is again estimated based on the estimated current variance. In this manner, by alternately estimating current distribution and current variance, appropriate values of J and $\alpha$ are obtained.

Also, when the current variance is estimated, "activity information obtained by fMRI", or information such as "current intensity correlation is strong between dipoles that are physically close to the point where the brain tends to act locally", and "estimation on the far side of the brain is not performed" are given as prior probabilities with respect to $\alpha^{-1}$, thereby increasing the probability that the current intensity at these dipoles is zero. With respect to a current source having $\alpha^{-1}$ of a large value, sparsification is performed as necessary. In this experiment, the number of points of current sources are reduced from several tens of thousands to 2223 as a result of sparsification, and estimated current is obtained for the reduced current sources. Note that although the prior probabilities include the activity information obtained by fMRI, even if erroneous information by fMRI is included, current sources can be estimated appropriately with the use of observed data.

Data of nine experiment days from October to December was used for analysis with respect to one of the subjects (hereinafter referred to as "Subject 1"), and data of four experiment days in or after December was used for analysis with respect to the other subject (hereinafter referred to as "Subject 2"). With respect to the analysis for Subject 1, an analysis parameter for selecting feature amount is decided based on the data of experiment days by November. With respect to Subject 2, since there is not sufficient amount of data for selecting a parameter based on tendencies, other than the abnormal data removing processing performed by the abnormal data removing unit 1011, the parameter of Subject 1 was applied.

The spatial filter used for current source estimation is calculated using experiment data of the 1st to 10th run. With respect to the data used for the test of 11th to 15th runs as well, estimated current on the brain surface was calculated using the spatial filter created based on the data of the 1st to 10th run, and learning and discrimination were performed. Note that in the current source estimation, if a large amount of signals other than brain waves is included in data used for calculating the spatial filter as described above, an adverse effect may occur to the estimation result, and thus data that is considered to include noises or artifacts was discarded in advance. Abnormal data removal for discarding such data is performed by the abnormal data removing unit 1011.

Here, the concept of the abnormal data removing processing performed by the abnormal data removing unit 1011 will be described (FIG. 16). First, in the brain information output apparatus 21, brain activity data of a user (S11) is measured by a brain activity measurement device (S13) including a plurality of sensors (S12), and row brain activity data 1 (measurement data 1) is obtained. Here, the brain activity measurement device (S13) corresponds to the first learning data acquiring unit 1012. Note that the measurement data 1 is composed of a plurality of trial data (a series of data) obtained when a certain operation (for example, moving the body, imagining, or the like) is performed once. Also, the brain activity data 1 (measurement data 1) is, for example, brain wave data. Also, the trial data is constituted by time-series data from the plurality of sensors (S12) provided in the brain activity measurement device (S13). From the brain activity data 1, the sensor data including an external noise or abnormal noise is removed by an abnormal sensor removing device (S14). Here, the abnormal sensor removing device (S14) corresponds to the abnormal sensor removing section 10112.

Also, trial data including a plurality of abnormal noises is removed by an abnormal trial removing device (S15). Here, the abnormal trial removing device (S15) corresponds to the abnormal trial removing section 10111.

Abnormal data is removed by the abnormal sensor removing device (S14) and the abnormal trial removing device (S15), and thereby normal brain activity data (normal data 3) is obtained. The normal data 3 corresponds to normal learning data.

In the brain information output apparatus 21, various parameters (S17) in an intention detection algorithm (S16) are adjusted by applying the normal data 3 to the intention detection algorithm. The brain information output apparatus 21 can provide a high-performance Brain Machine Interface due to the adjusted parameters (S17) and the intention detection algorithm (S16). Note that the intention detection algorithm corresponds to the intention identifier acquiring unit 1019. Also, the parameters (S17) corresponds to the learning feature amount group.

It is assumed that the first learning data acquiring unit 1012 includes a plurality of sensors, and acquires brain wave data and NIRS data from the brain of the user. That is, the first learning data acquiring unit 1012 corresponds to a brain wave measuring apparatus and an NIRS measurement apparatus. Note that here, the processing for removing abnormal data from the brain wave data will be described.

Then, it is assumed that the first learning data acquiring unit 1012 has acquired the brain wave data shown in FIG. 17. This brain wave data includes time-series data of brain waves acquired from six sensors. Then, the first learning data acquiring unit 1012 temporarily accumulates the acquired learning data (FIG. 17) in a recording medium.

Next, the brain information output apparatus 21 performs processing for removing abnormal data from the first learning data shown in FIG. 17. That is, the abnormal data removing unit 1011 performs processing for removing abnormal data through the following steps ((1) to (8)), for example. Here, the abnormal data removing processing will be described with reference to the conceptual diagram in FIG. 18.

(1) The abnormal data removing unit 1011 acquires the entire time-series data for each sensor. Then, the abnormal data removing unit 1011 calculates, for each sensor, a mean value and a standard deviation $\sigma$ for the entire time-series data. Here, the entire time-series data refers to the data covering all the trials.

(2) The abnormal data removing unit 1011 sets the mean value of the respective sensor data sets and the respective trial data sets (FIG. 18($a$)) as a reference point. Reference correction is performed on the time-series data of brain waves and then the entire time-series data is squared, thereby calculating the powers of the signals (FIG. 18($b$)). The acquired data is three-dimensional data (a plurality of sensors×time series×a plurality of trials).

(3) The abnormal data removing unit 1011 calculates distribution with respect to the powers of signals. Note that this distribution is generally obtained according to X square distribution. The top 5% of the samples in terms of largest value is discarded (FIG. 18($c$)). The top 5% of the samples in terms of largest value is regarded as noise that may occur in a normal condition, and thus discarded.

(4) The abnormal data removing unit 1011 discards the 5% of the samples, and obtains a largest power $P_{95}$ using the absolute values of the remaining data sets.

(5) The abnormal data removing unit 1011 calculates, for each trial of each sensor, a value $m_{amp}$ that is obtained by dividing the power $P_{95}$ by the standard deviation $\sigma$, thereby obtaining the matrix shown in FIG. 18($d$).

(6) The abnormal data removing unit 1011 compares a predetermined constant "a" for removing abnormal data with the matrix, and obtains $m_{amp}$ that is larger than "a". "9" is preferable as the value of the constant "a". Also, in FIG. 18($d$), data sets marked with a diagonal line in the matrix correspond to samples that have been removed as inappropriate data.

(7) The abnormal data removing unit 1011 counts, for each sensor, the number of inappropriate data sets in the trial direction. This number is indicated by $b_{sensor}$. Here, counting in the trial direction for each sensor means counting, for each sensor, the number of inappropriate data sets marked with a diagonal line in the lateral direction in FIG. 18($d$). Also, the abnormal data removing unit 1011 counts, for each trial, the number of inappropriate data sets in the sensor direction. This number is indicated by $b_{trial}$. Here, counting in the sensor direction for each trial means counting, for each trial, the number of inappropriate data sets marked with a diagonal line in the longitudinal direction in FIG. 18($d$).

(8) The abnormal data removing unit 1011 compares a predetermined constant $c_{sensor}$ for removing abnormal data with the $b_{sensor}$, and if the $b_{sensor}$ is larger than the $c_{sensor}$, the corresponding sensor is determined to have an abnormality, and the data acquired by that sensor is removed as an abnormal sensor (hereinafter referred to as "abnormal sensor removal"). Here, the predetermined constant $c_{sensor}$ is preferably a value that corresponds to approximately 5% of the total number of trials. Also, the abnormal data removing unit 1011 compares a predetermined constant $c_{trial}$ for removing abnormal data with the $b_{trial}$, and if the $b_{trial}$ is larger than the $c_{trial}$, the corresponding trial is determined to have an abnormality, and the data acquired by that trial is removed as an abnormal trial (hereinafter referred to referred to as "abnormal trial removal"). Here, the predetermined constant $c_{trial}$ is preferably a value that corresponds to approximately 5% of the total number of sensors.

Note that the abnormal data removing unit 1011 may re-count the $b_{trial}$ after the abnormal sensor removal, or may re-count $b_{sensor}$ after the abnormal trial removal. At this time, the abnormal sensor removal and the abnormal trial removal may be performed in any order, and the abnormal sensor removal and the abnormal trial removal may be repeated a plurality of times.

With the above-described processing, the abnormal data removing unit 1011 can remove abnormal data from the learning data and acquire normal learning data. Specifically, the abnormal data removing unit 1011 acquires feature values (the number of samples that exceeds $m_{amp}$-fold with respect to the standard deviation, the number of samples that exceeds $m_{diff}$-hold with respect to the standard deviation (border value), or the like) of one or more partial learning data sets (a partial learning data set is a set of samples of one sensor, or a set of samples of one trial), determines whether each partial learning data is normal or abnormal using the corresponding feature value, removes the partial learning data determined to be abnormal from the learning data, and thereby acquires normal learning data. Next, the abnormal data removing unit 1011 temporarily accumulates the normal learning data, which is obtained as a result of the abnormal data removing processing.

Also in the experiment, the feature amount was determined as described below. Specifically, in the experiment, activity at 2233 current sources are estimated with the use of an EEG having 64 channels. Also, with respect to the feature amount used for discrimination, learning and determination is performed based on the power of a frequency band of the estimated current. However, if it were to form combinations of the estimated 2233 current sources and a plurality of frequency bands, the number of the feature amounts will be numerous. If learning is performed using such a large number of feature amounts, reduction in generalization due to over-learning may occur, although occurrence of such reduction depends on the discriminator. Therefore, such learning is practically difficult in terms of calculation cost as well.

Accordingly, in order to prevent these problems, it is necessary to extract only effective feature amounts in advance. In the experiment, as a method for extracting feature amounts, multiple testing was performed first, and then current sources and frequency bands showing a large difference between tasks were selected. Thereafter, with a learning device, feature amounts is further narrowed down using the above-described abnormal data removing unit 1011 (Sparse Logistic Regression).

The powers of the frequency component were used as the feature amounts. However, in the scheme of this experiment, it is difficult to know a clear onset position with respect to the image, and thus the average of the power for the all intervals of the task was used.

Next, the procedure of multiple testing will be described. In order to perform multiple testing, the following variables are defined.

n: current source number
N: total number of current sources
l: task label number
L: type of task label
f: frequency band [Hz]
$m_l$: trial number assigned with task label l
$M_l$: total number of trials assigned with task label l P (f, n, l, $m_l$) is defined with these variables. P (f, n, l, $m_l$) is obtained in the procedure described below (see FIG. 19).

(1) Signal in the $m_l$-th task interval assigned with the task label l: l∈{1, 2, 3, 4} is extracted with respect to the estimated current at the n-th current source.
(2) Frequency conversion is performed on the extracted signal, and the power is calculated.
(3) The power corresponding to the band f [Hz] is defined as P (f, n, l, $m_l$).

Multiple testing is performed in the following procedure on the P (f, n, l, $m_l$) obtained as described above. Note that this procedure is schematically illustrated in FIG. 20.

(4) An average P-bar (f, n, l) of all trials is obtained with respect to P (f, n, l, $m_l$). Note that "P-bar" refers to a sign formed by placing the sign "-" above the letter "P".

(5) With respect to each combination of tasks $l_i$ and $l_j$ (six combinations in total, as obtained by $_4C_2$), t-test is performed while taking variance thereof into consideration (see Expression 11).

$$t_{(l_i, l_j), f} = \frac{\overline{P}(f, n, l_i) - \overline{P}(f, n, l_j)}{\sqrt{V_w \left( \frac{1}{M_{l_i}} + \frac{1}{M_{l_j}} \right)}} \quad \text{[Expression 11]}$$

Here, $V_w$ is the error variance, which can be expressed as in Expression 12 using the variance $\sigma(P(h, n, l, m_l))^2$ of P (f, n, l, $m_l$) in the same task.

$$V_w = \frac{\sum_l ((M_l - 1) \times \sigma(P(f, n, l, m_l))^2)}{\sum_l M_l - L} \quad \text{[Expression 12]}$$

(6) Next, a sum $t'_{l_i, l_j}$ of statics $t_{l_i, l_j}$ that are obtained under the same combination and for all frequency bands is obtained (see Expression 13).

$$t'_{n(l_i, l_j)} = \sum_k t_{(i,j), f_k} \quad \text{[Expression 13]}$$

(7) $t'l_i, l_j$ is obtained for all current sources, and for each combination of i and j, the top $n_{select}$ number of current sources in terms of largest value of $t'l_i, l_j$ are selected as feature amounts.

By this selection of the current sources based on the multiple testing, current sources that tend to averagely show a difference over all frequency bands can be selected with respect to a combination of specific tasks. The outline of the procedure described thus far is shown in FIG. 20.

In addition, instead of $t'_{n(li, lj)}$ obtained in the above case from the sum for all frequency bands, this time, $t'_{f(li, lj)}$, which is a sum for all the current sources, is obtained in a similar manner. With respect to estimated currents from the same current source, a frequency band in which the difference between tasks is large has a large the value of $t'_{f(li, lj)}$. Also in this case, the top $n_{select}$ number of frequency bands in terms of largest value are selected as frequency bands in which the difference between tasks is large.

Parameter $n_{select}$ necessary for the selection based on multiple testing is set as "$n_{select}$=20", as a result of verification using experiment data for eight days of Subject 1 measured in September, which is not used for testing or learning, and selection was performed for each of the entire brain, right and left hemispheres of the brain.

Using the combinations of the current sources and the frequency bands defined in this manner as feature amounts, learning and discrimination were performed using Sparse Logistic Regression.

(Results of Experiment)

The results of each experiment day of discrimination performed based on the mapping on the brain surface, and the results that were obtained, for the purpose of comparison, by performing multiple testing on brain waves measured on the scalp in the same manner as that used for the estimated current, selecting sensors and frequency bands considered to be effective as feature amounts, and performing discrimination at the sensor level are shown.

(1) Subject 1

FIGS. 21 and 22 show the discrimination results for nine days with respect to Subject 1. Based on these experiment results, as a result of performing t-test under a null hypothesis that the two discrimination cases have an equal correct rate, this null hypothesis was denied at the significance level of 5%. Thus, it is possible to consider that estimation of current source is generally effective for discrimination, and improves discrimination performance. Also, with respect to the correct rate, kappa statics of 0.5 to 0.8 were obtained, which can generally be regarded as high matching ratios.

(2) Subject 2

When analysis was performed with respect to Subject 2 using the same parameter, most data of Subject 2 was discarded as "Bad Sensor" that includes noises or artifacts. This may be because the standard of Subject 1, who can undertake experiment in a relatively stable condition, was too strict for Subject 2, who has little experience of this kind of experiment.

Therefore, in order to remove artifacts caused by a large motion of the body, a high-pass filter of 1 Hz was used. As a result, since estimation results having a certain level of reliability were obtained without removal processing, estimation and learning were performed without performing the removal processing with respect to the sensors and the trials.

Similar to the case of Subject 1, discrimination results are shown in FIGS. 23 and 24 along with the results obtained by performing multiple comparison on the data obtained by the sensors of EEG.

As a result of performing t-test in a similar manner, difference in the correct rate could be proved at the significance level of 5%. It is found that the results of Subject 2, who has less experience of BMI experiment than Subject 1, have a larger difference from the data obtained by the EEG than that of Subject 1.

As described above, according to the present embodiment, it is verified that the motion image discrimination performance can be improved by estimating current sources using the hierarchical variational Bayes approach. Also, as an observation, performance comparison was performed according to the distribution of current sources that contributed to discrimination and the number of times of learning. Note that in the observation described below, observation was performed for Subject 1 due to the number of data sets.

(Distribution of Current Sources That Contributed to Discrimination)

In this experiment, the power of a specific frequency band of the estimated current of a certain current source is used as the feature amount, as described above, and as a result of multiple analysis or sparsification, current sources are narrowed down so that approximately 60 current sources finally remain to be weighted for each day.

FIG. 25 shows current sources that finally remained to be weighted as a result of this analysis. In Sparse Logistic Regression, binary determination between one task against other tasks, is performed for each of the four tasks, and in the course of the binary determination, current sources that do not make much contribution to the determination are sparsified.

That is, regions in the Brodmann Area where different tendencies were shown depending on the tasks can be recognized in FIG. 25. According to FIG. 25, it can be understood that the current sources in Areas 3, 5 and 7 contribute to the determination. Here, the functions of Areas 3, 5 and 7 are described. Areas 1 to 3 are classified as the primary somatosensory area, and are said to have a function of receiving information from the skin or the joints. Also, similar to the motor area, Homunculus model is established in Areas 1 to 3, and thus it is highly conceivable that classification of activities according to the positional information of the activities becomes possible. Areas 5 and 7 both correspond to the parietal association area, and in particular, Area 7 is regarded as a region where spatial recognition is performed in association with visual perception. These sensory area for receiving sensory information and parietal association area that functions when the received information is exchanged with a region having another function are essential for motion. The relation between these regions and the motor learning has been pointed out also in experiments using monkeys.

In this experiment, it can be understood that sparsification was performed considering that signals estimated to correspond to a region that may have a large relation to the corresponding tasks make a large contribution to the determination, and that estimated currents in a region that may have a relatively small relation do not contribute to determination.

Also, more specifically, the selection frequency for nine experiment days was checked for each current source. FIG. 26 shows, in a histogram, the current sources that were selected in plural experiment days, out of 296 current source points that serve as the feature amounts and made contribution to the determination in any of nine experiment days. Out of 2233 current source points, only one current source was selected in more than half of the experiment days, and not less than 70% of the current sources were selected only once during nine experiment days. Based on this, as a result of this estimation, although common tendencies can be seen over plural experiment days at the level of region, which is a relatively large classification, at the level of the individual estimated current source points, common tendencies cannot be seen.

(Relation Between Number of Times of Learning and Discrimination Performance)

With respect to the relation between the number of times of learning and the discrimination performance, generally, discrimination performance improves with an increase of the number of times of learning, once a certain number of times of learning has been reached, and in contrast, once the discrimination performance has reached a certain level, the improvement ratio of performance relative to the number of data sets gradually approaches zero. In this experiment, a description has been given using a case in which the number of times of learning is 70 trials for each task, namely, 280 trials in total, which correspond to 10 runs of the paradigm of this experiment. Change in the determination performance caused by a change in the number of times of learning was observed.

In comparison to the above-described learning based on the data of 280 trials corresponding to 10 runs, learning is performed with 140 trials corresponding to 1st to 5th runs and with 224 trials corresponding to 1st to 8th runs, in the same order as that in the measurement on the experiment days. For both cases, testing was performed with 11th to 15th runs. Note that learning referred to here also serves as learning data used for calculating a conversion matrix for estimating current sources, and thus for example, under the condition of learning data of 140 trials, the estimation of current sources is also performed based on the data of 140 trials. Also, the thresholds for Bad Sensor are respectively set to values proportional to the number of learning data sets.

Determination results obtained with the respective numbers of the learning data are shown in FIGS. 27 and 28. With an increase in the number of times of learning, both the correct rate in discrimination and the standard deviation are improved. Even with the results of the testing based on the smallest number of times of learning (140 trials for 5 runs (35 trials for each task)) in this observation, the correct rate of at least 66% was obtained.

(Conclusion)

Motor image experiment for right hand, left hand, tongue and foot was performed on two subjects, and the brain waves measured and currents estimated from the brain waves at the experiment were discriminated in the same method. As a result, a significant improvement in discrimination performance was recognized for both subjects. The average discrimination ratios for the two subjects are 72.85% and 68.44%, respectively, and with respect to the kappa statics as well, the results of the two subjects are 0.63 and 0.58, respectively, and generally, sufficient matching is achieved for Subject 1. Although sufficient matching could not be achieved for Subject 2, a high matching level was achieved. Also, it is possible to say that these discrimination results represent the highest level of correct rates in BMIs currently available in the world.

FIG. 29 shows the external appearance of a computer that executes the programs referred to in the specification to realize the brain information output apparatus, and the like in the foregoing embodiments. The foregoing embodiments may be realized using computer hardware and a computer program executed thereon. FIG. 29 is a schematic diagram of a computer system 340. FIG. 30 is a block diagram of the computer system 340.

In FIG. 29, the computer system 340 includes a computer 341 including an FD drive and a CD-ROM drive, a keyboard 342, a mouse 343, and a monitor 344.

In FIG. 30, the computer 341 includes not only a FD drive 3411 and a CD-ROM drive 3412, but also a RAM 3416 that is connected to an MPU 3413, a bus 3414 that is connected to the CD-ROM drive 3412 and the FD drive 3411, and a ROM 3415 in which a program such as a startup program is to be stored, and in which a command of an application program is temporarily stored and a temporary storage area is to be provided, and a hard disk 3417 in which an application program, a system program, and data are to be stored. Although not shown, the computer 341 may further include a network card that provides connection to a LAN.

The program for causing the computer system 340 to execute the functions of the brain information output apparatus, and the like in the foregoing embodiments may be stored in a CD-ROM 3501 or an FD 3502, which are inserted into the CD-ROM drive 3412 or the FD drive 3411, and may be transmitted to the hard disk 3417. Alternatively, the program may be transmitted to the computer 341 via a network (not shown) and stored in the hard disk 3417. At the time of execution, the program is loaded into the RAM 3416. The program may be loaded from the CD-ROM 3501 or the FD 3502, or directly from the network.

The program does not necessarily have to include, for example, an operating system (OS) or a third party program to cause the computer 341 to execute the functions of the brain information output apparatus, and the like in the above-described embodiments. The program may only include a portion of command capable of calling an appropriate function (module) in a controlled mode and obtaining the desired results. The manner in which the computer system 340 operates is well known, and, thus, a detailed description thereof is omitted.

It should be noted that, in the program, a process performed by hardware, for example, a process performed by a modem or an interface card (a process that can be performed only by such hardware) is not included.

Furthermore, the computer that executes this program may be a single computer, or may be multiple computers. More specifically, centralized processing may be performed, or distributed processing may be performed.

Furthermore, in the foregoing embodiments, each process (each function) may be realized as an integrated process using a single apparatus (system), or may be realized as a distributed process using multiple apparatuses.

The present invention is not limited to the embodiments set forth herein. Various modifications are possible within the scope of the present invention.

INDUSTRIAL APPLICABILITY

As described above, the brain information output apparatus of the present invention can detect intentions with high accuracy, and can be used as a BMI or the like.

BRIEF DESCRIPTION OF THE DRAWINGS

FIG. 14 is a diagram illustrating a task performed by a subject in Embodiment 2.

FIG. 22 shows experimental results for Subject 1 in Embodiment 2.

FIG. 24 shows experimental results for Subject 2 in Embodiment 2.

FIG. 28 shows determination results in Embodiment 2.

Figure 1:
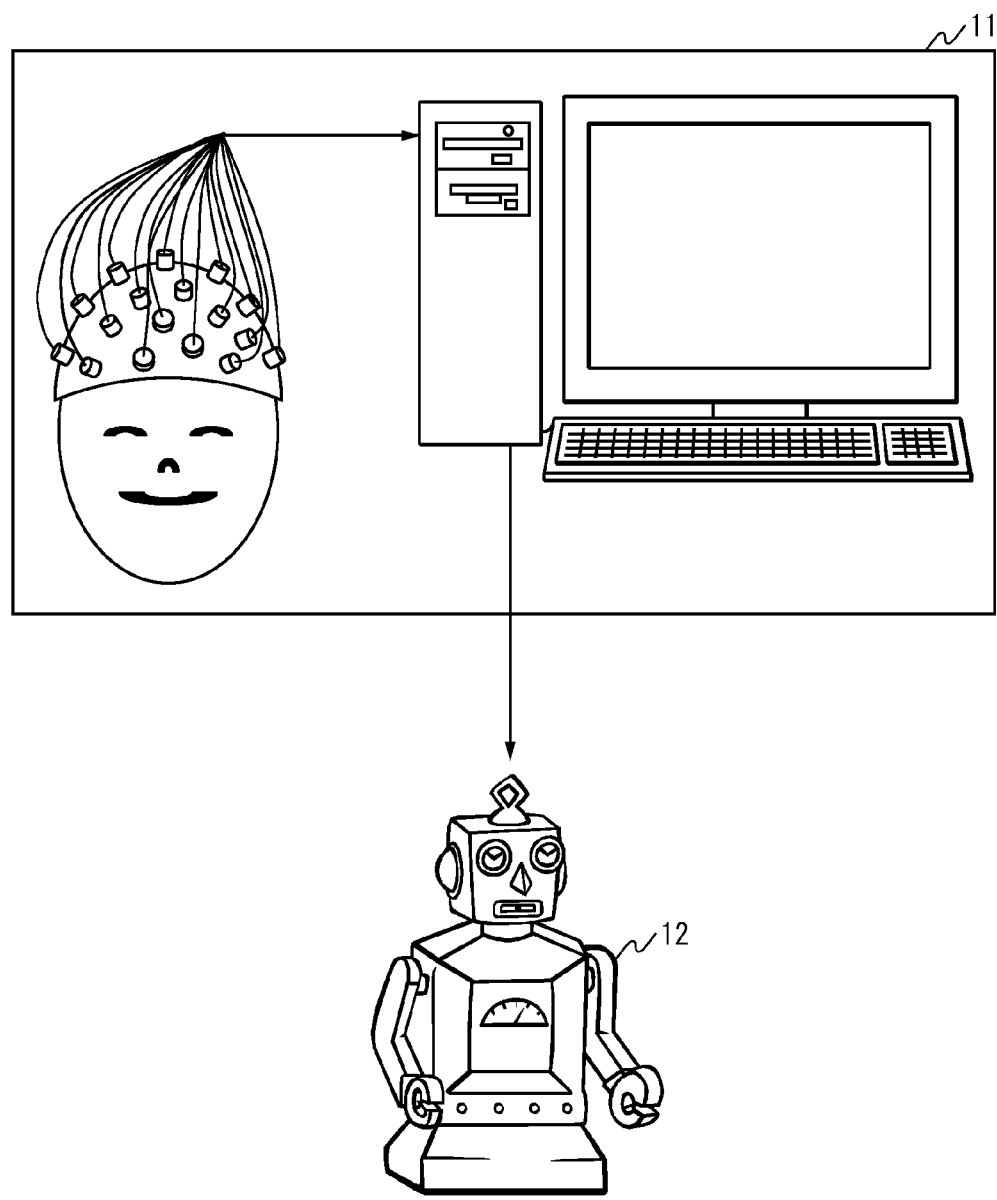
FIG. 1 is a conceptual diagram of a robot system 1 in Embodiment 1.
Figure 2:
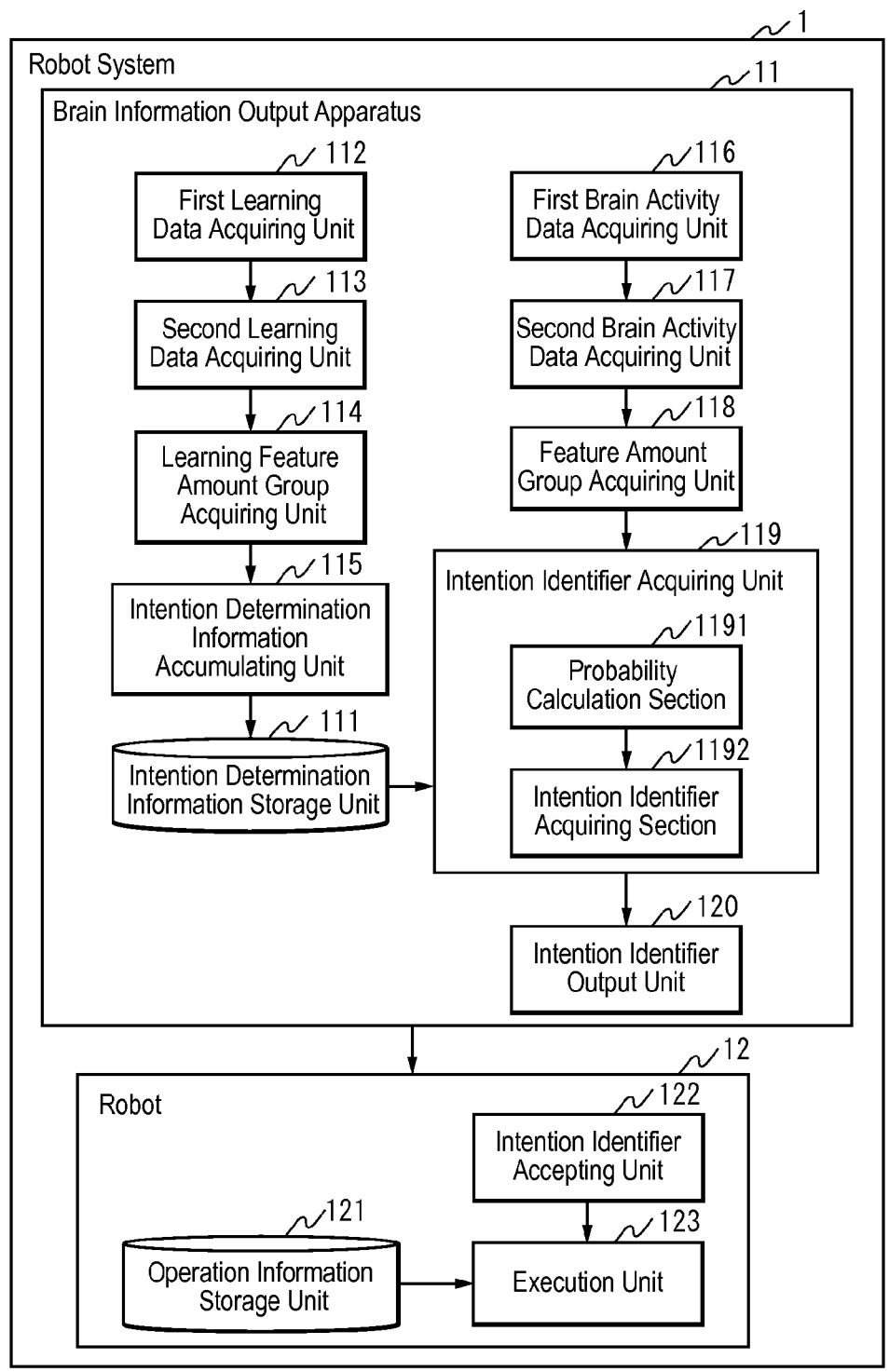
FIG. 2 is a block diagram of the robot system 1 in Embodiment 1.
Figure 3:
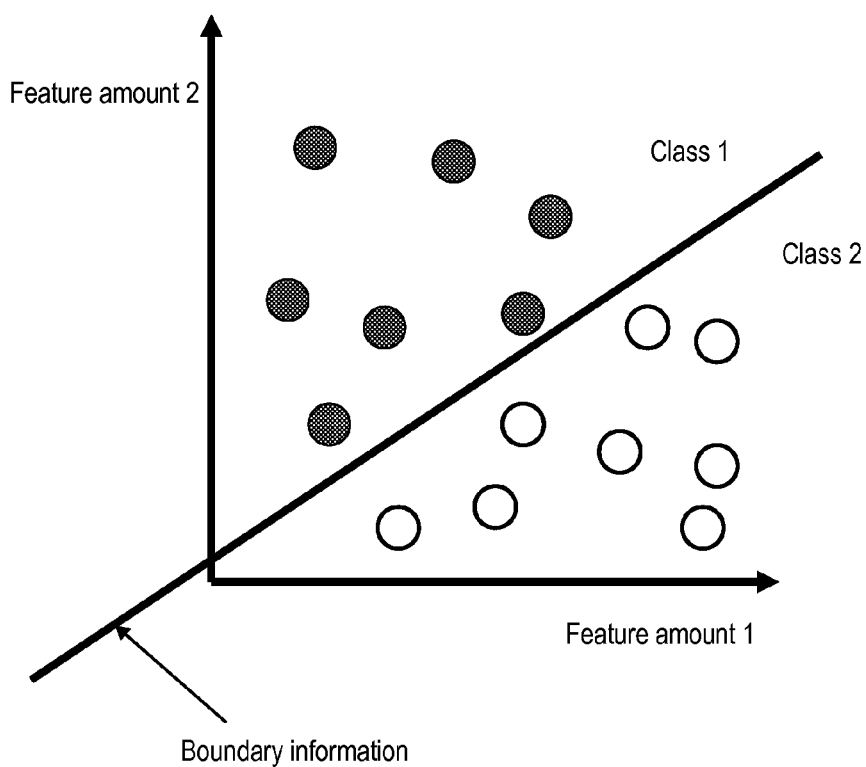
FIG. 3 is a diagram illustrating a probability calculation algorithm in Embodiment 1.
Figure 4:
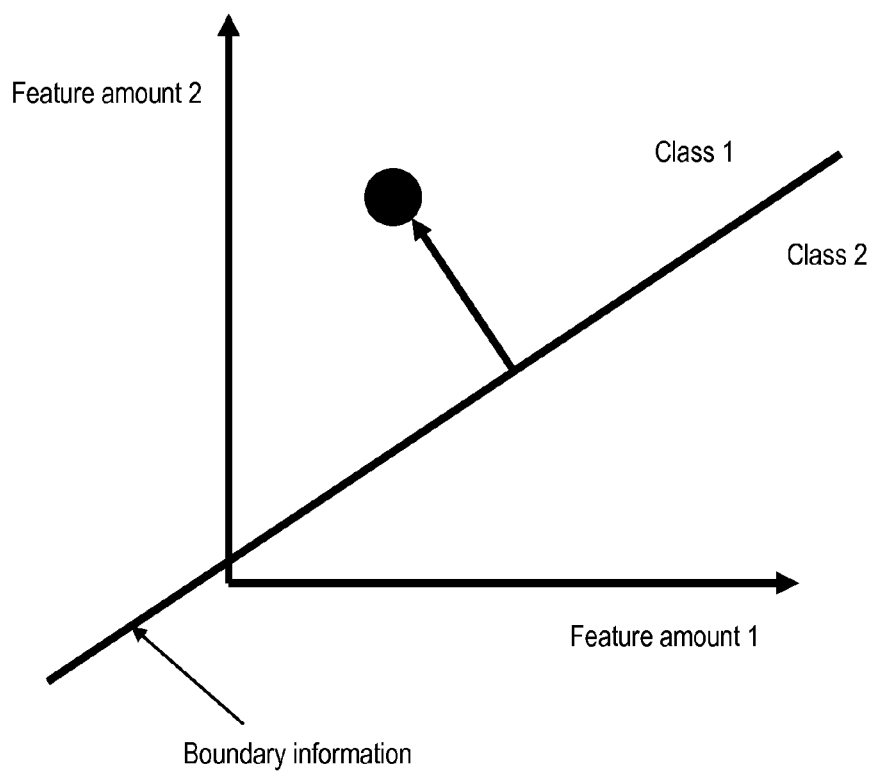
FIG. 4 is a diagram illustrating a probability calculation algorithm in Embodiment 1.
Figure 5:
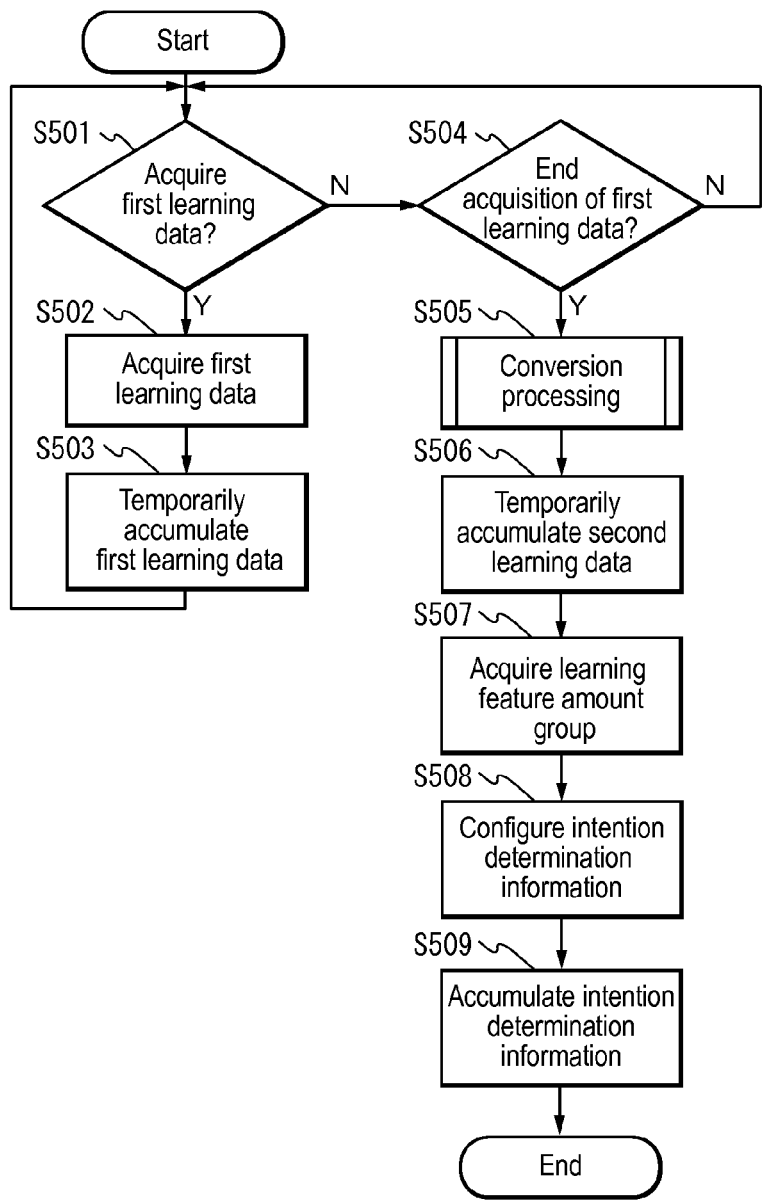
FIG. 5 is a flowchart illustrating an operation performed by a brain information output apparatus 11 in Embodiment 1.
Figure 6:
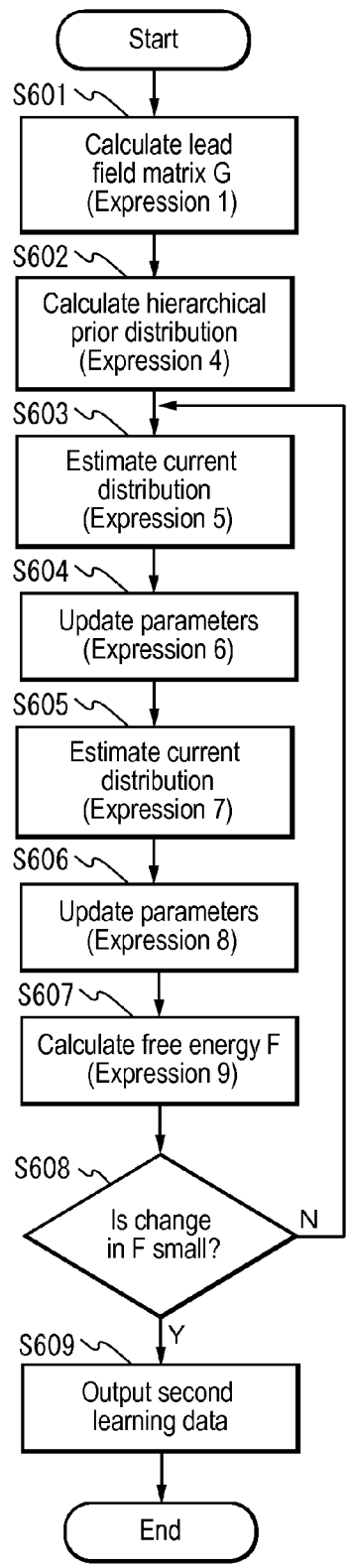
FIG. 6 is a flowchart illustrating conversion processing performed by the brain information output apparatus 11 in Embodiment 1.
Figure 7:
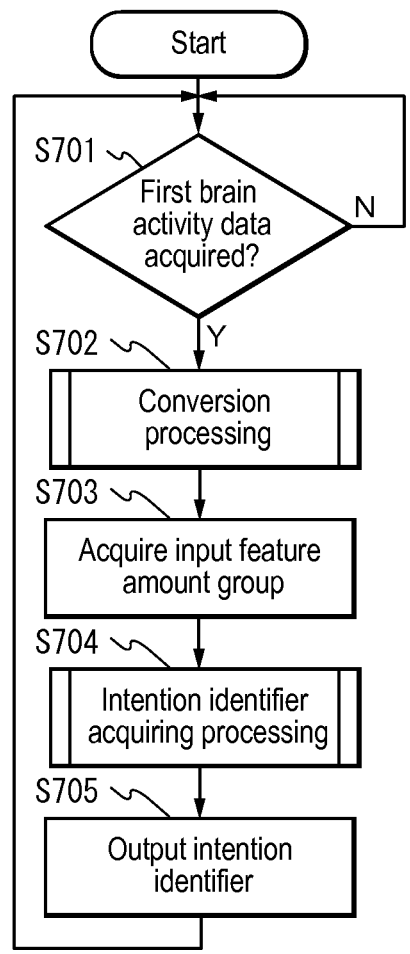
FIG. 7 is a flowchart illustrating intention identifier output processing performed by the brain information output apparatus 11 in Embodiment 1.
Figure 8:
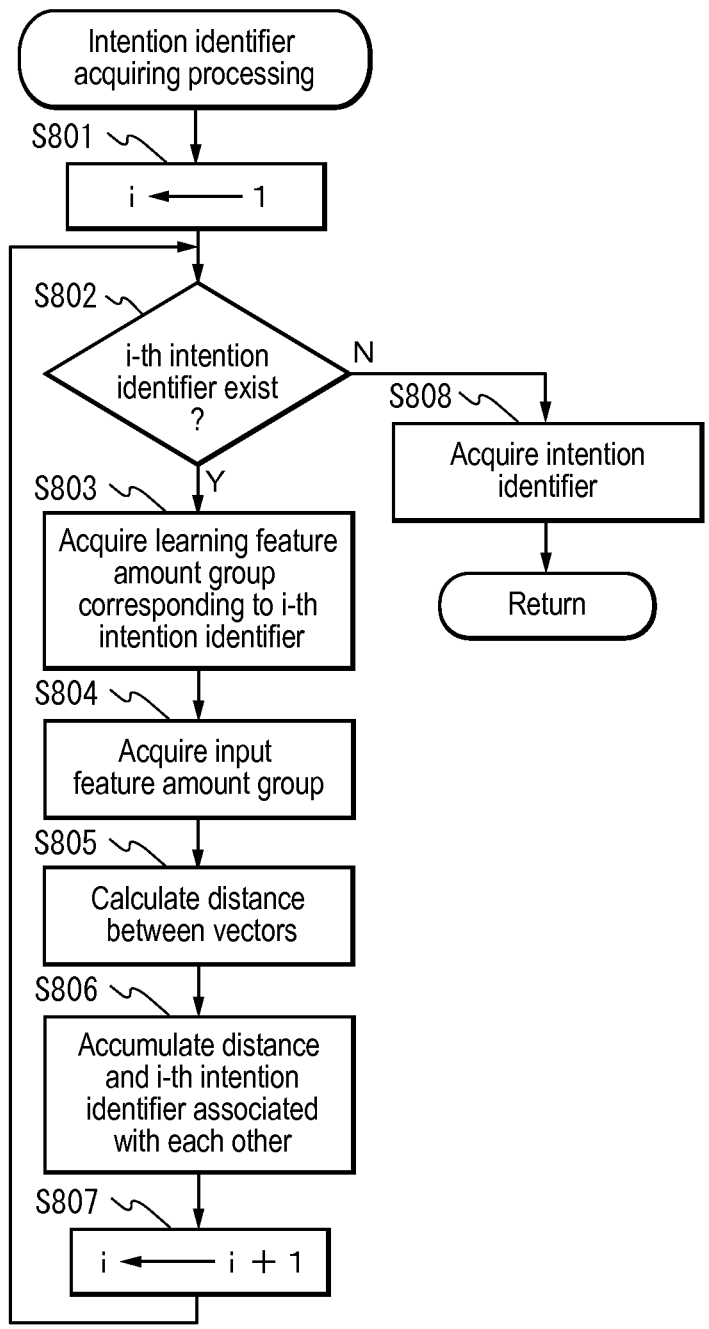
FIG. 8 is a flowchart illustrating intention identifier acquiring processing performed by the brain information output apparatus 11 in Embodiment 1.
Figure 9:
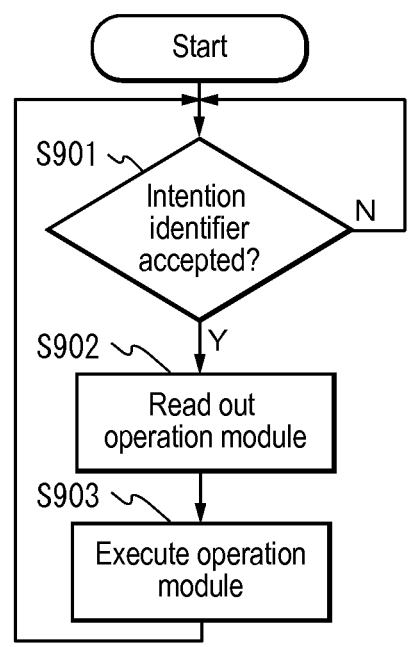
FIG. 9 is a flowchart illustrating an operation of a robot 12 in Embodiment 1.
Figure 10:
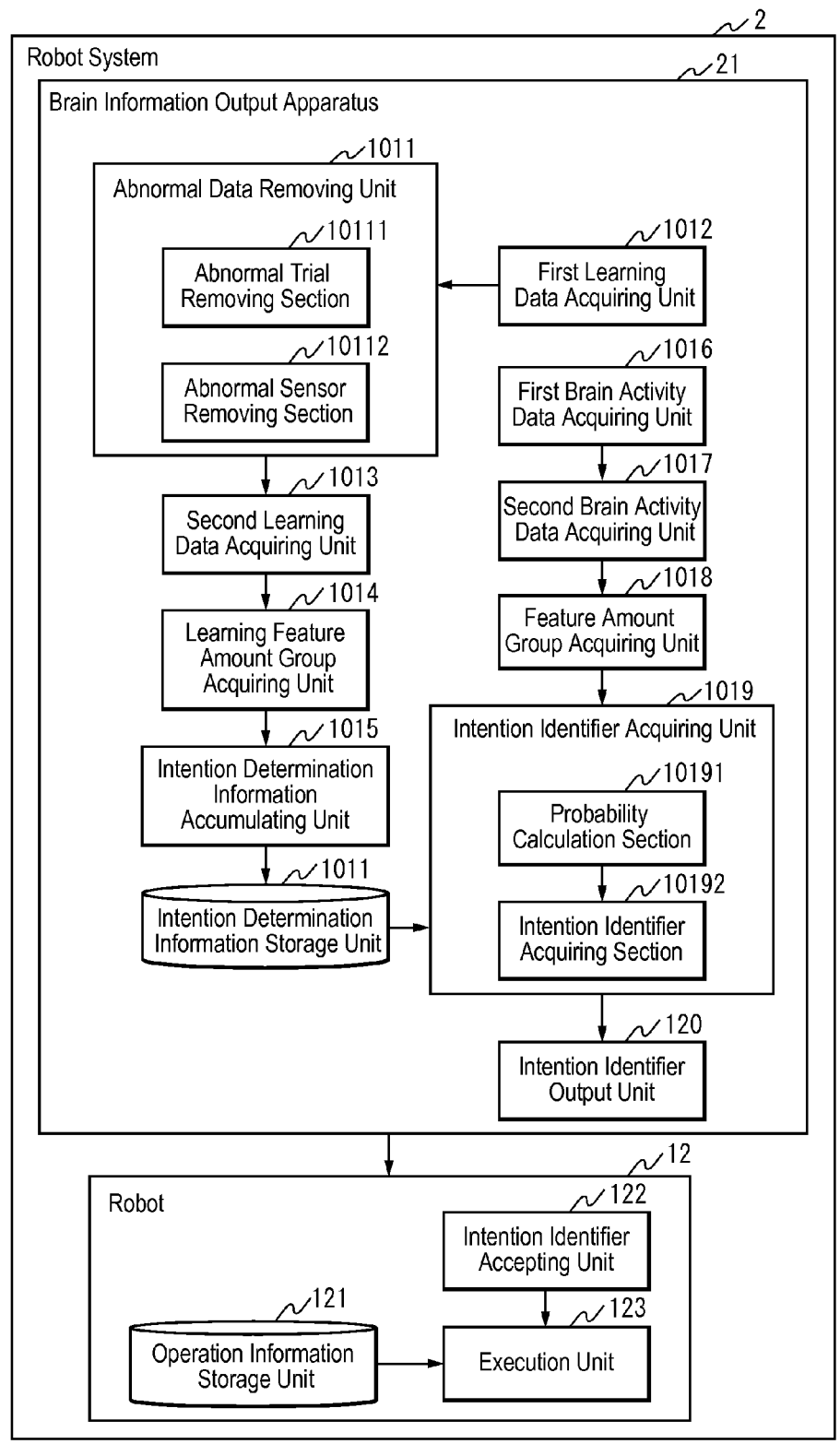
FIG. 10 is a block diagram of a robot system 2 in Embodiment 2.
Figure 11:
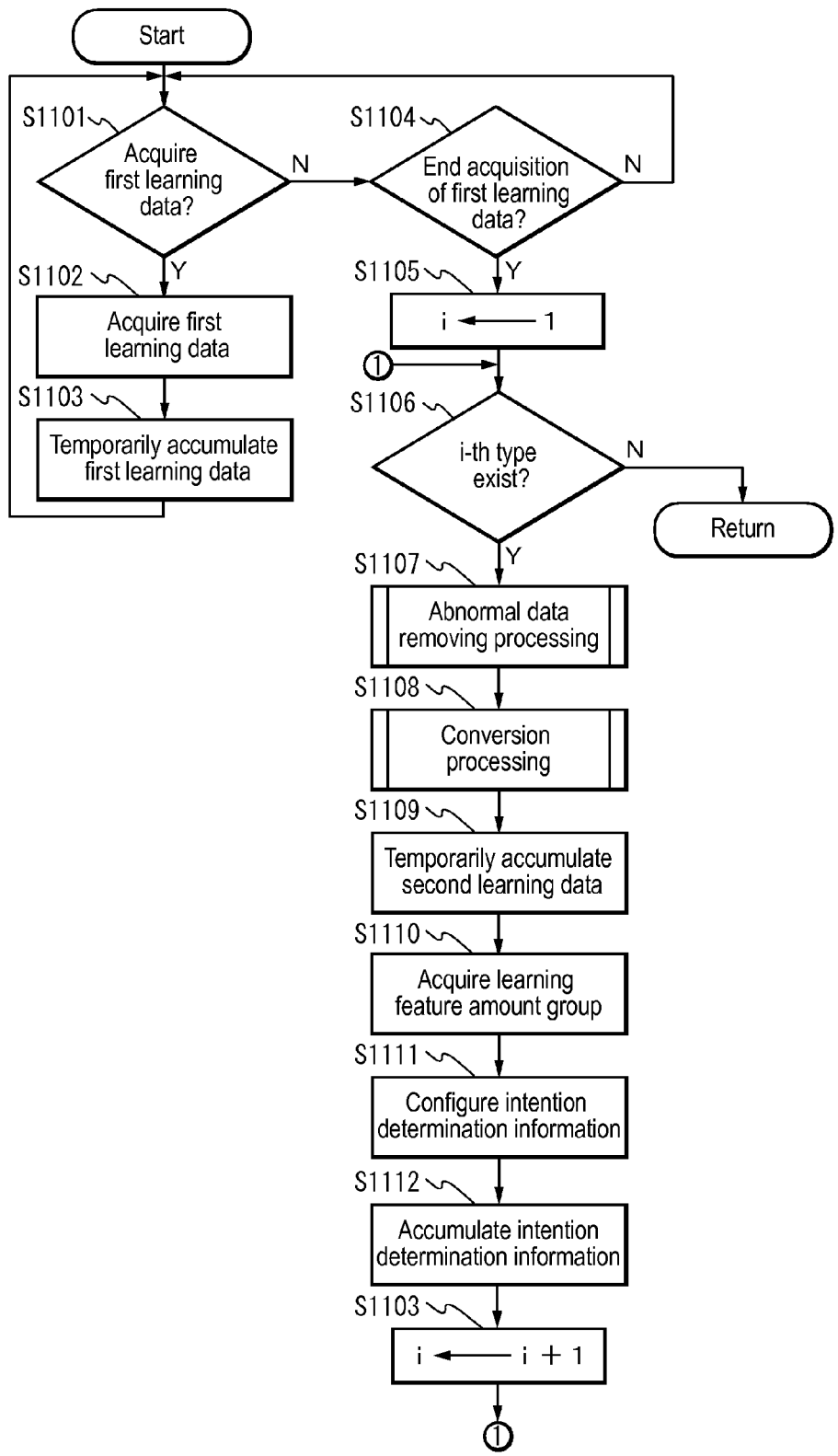
FIG. 11 is a flowchart illustrating an operation performed by a brain information output apparatus 21 in Embodiment 2.
Figure 12:
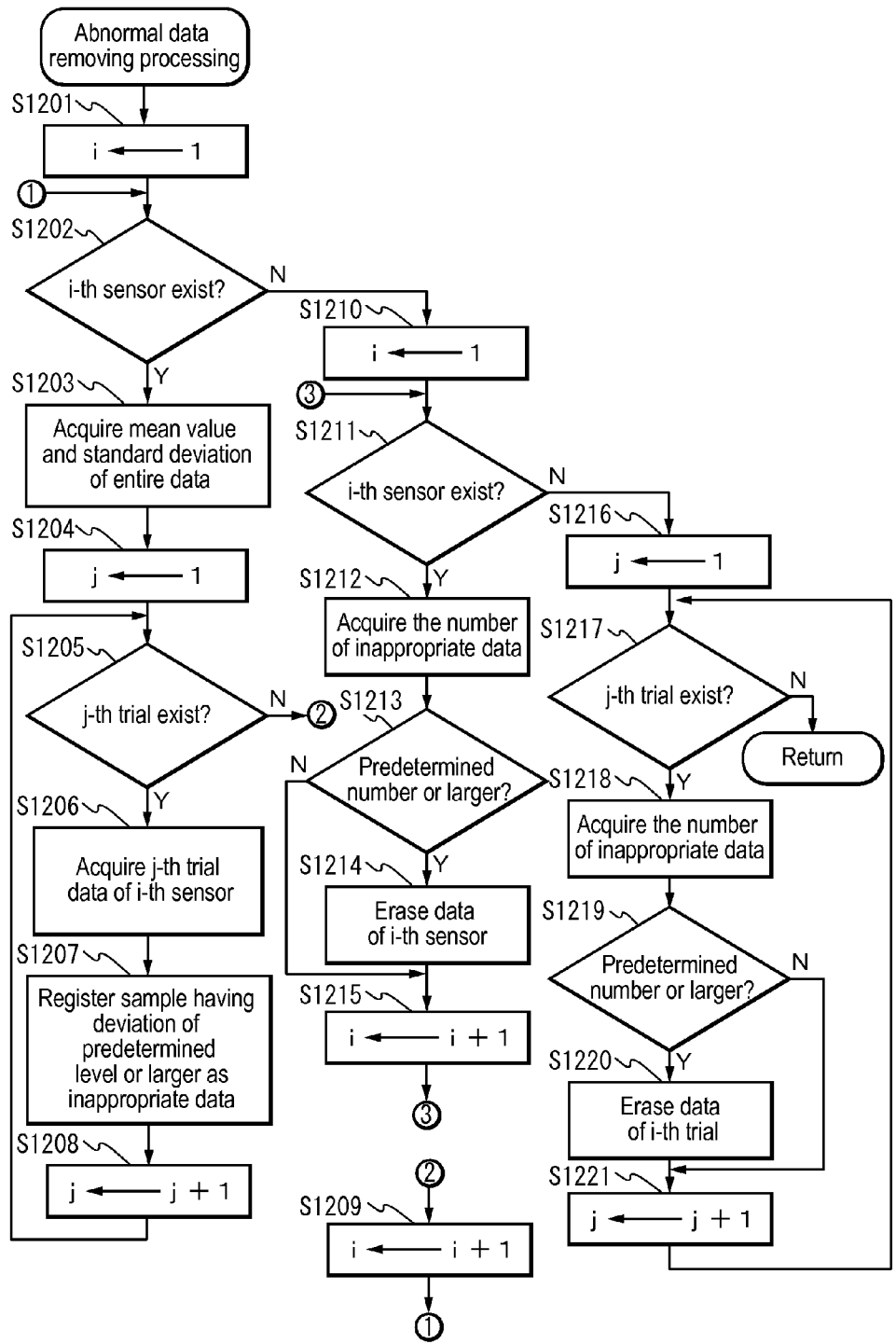
FIG. 12 is a flowchart illustrating abnormal data removing processing performed by the brain information output apparatus 21 in Embodiment 2.
Figure 13:
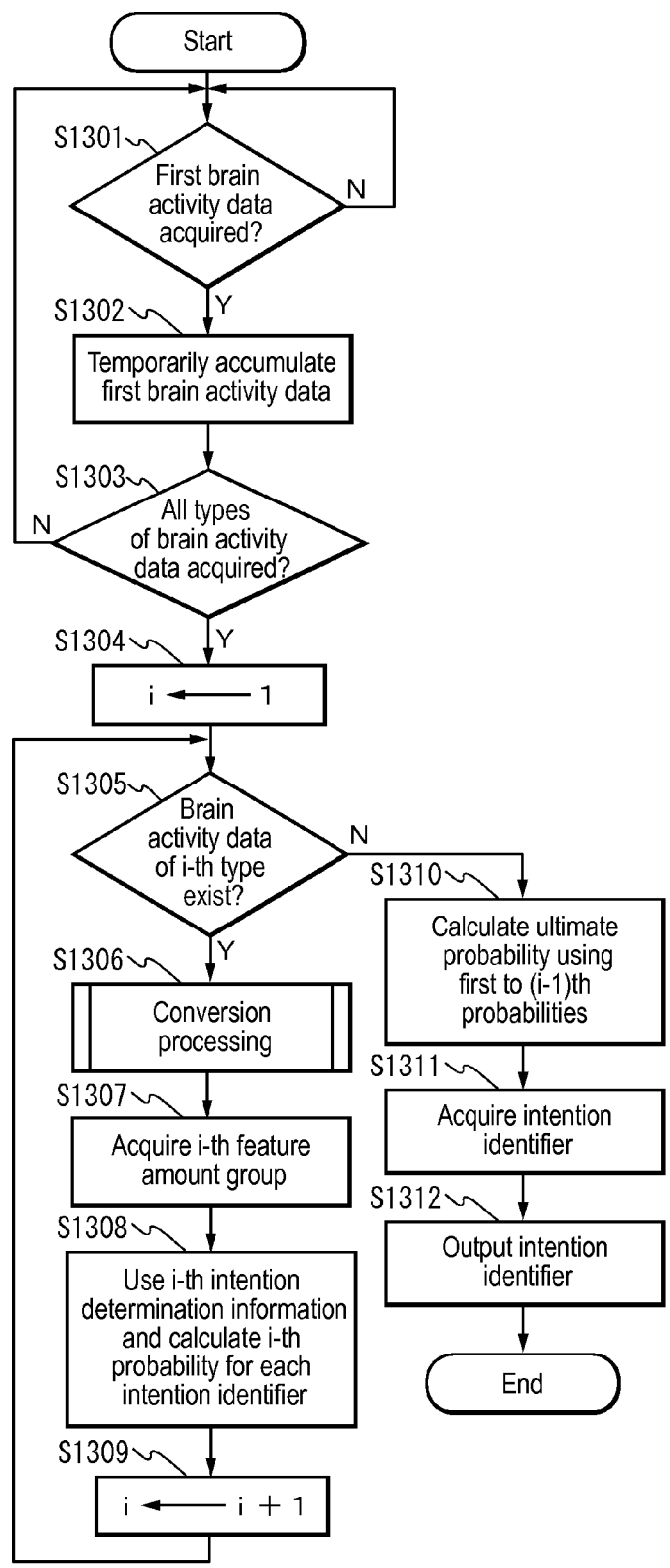
FIG. 13 is a flowchart illustrating intention identifier output processing performed by the brain information output apparatus 21 in Embodiment 2.
Figure 15:
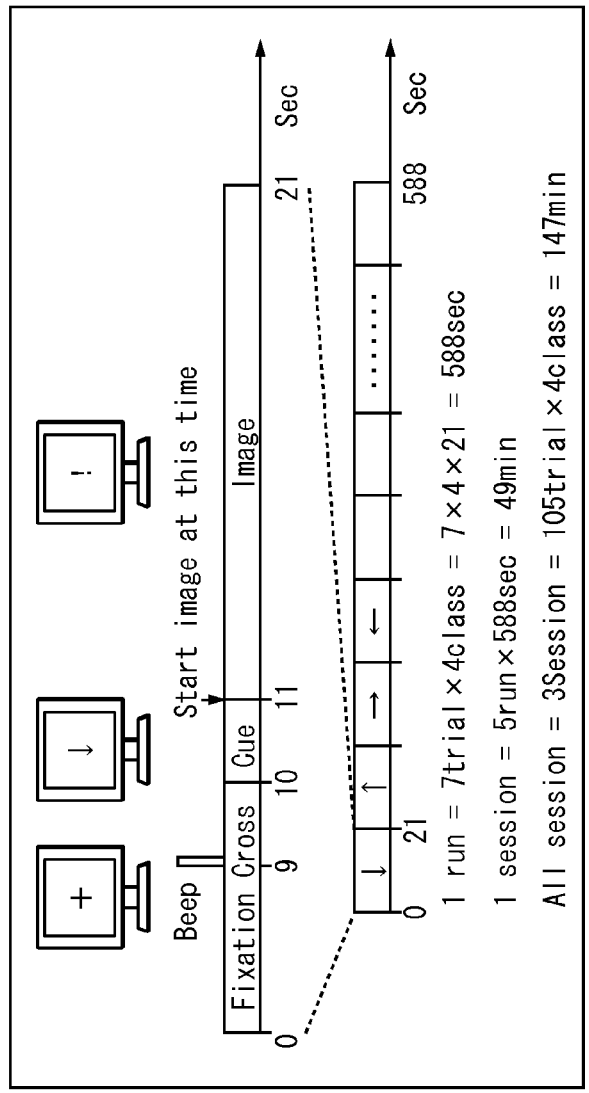
FIG. 15 is a diagram illustrating the flow of experiment in Embodiment 2.
Figure 16:
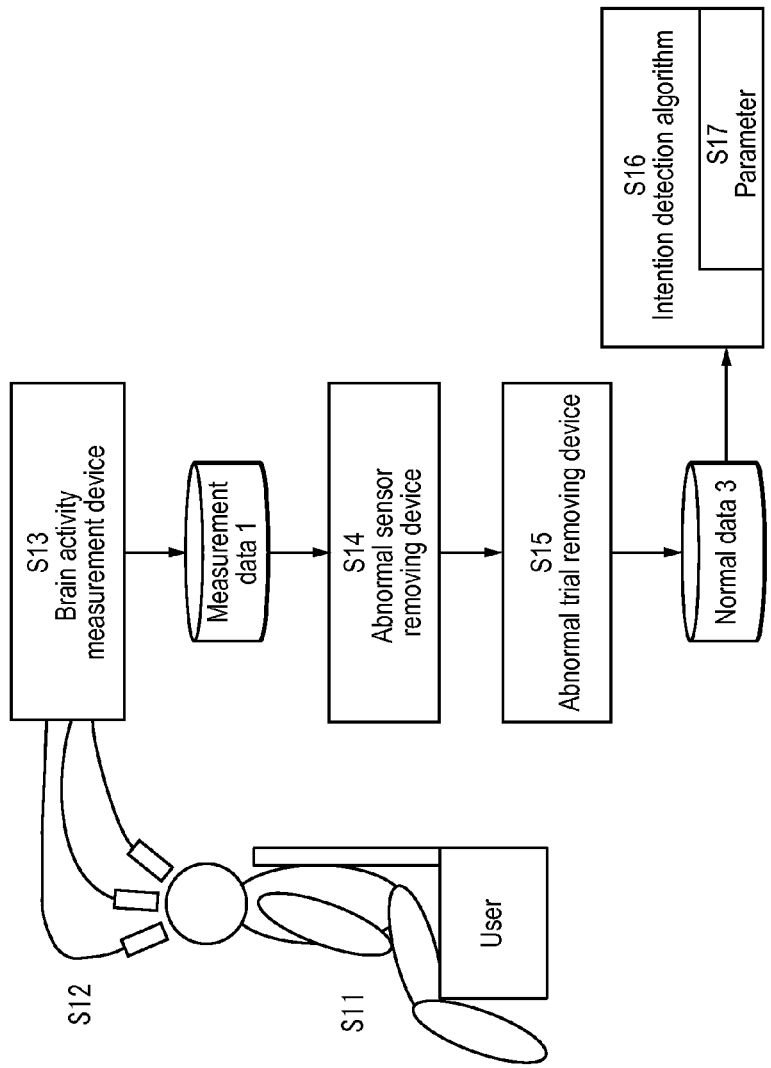
FIG. 16 is a diagram illustrating the concept of the abnormal data removing processing in Embodiment 2.
Figure 17:
FIG. 17 shows an example of brain wave data in Embodiment 2.
Figure 18:
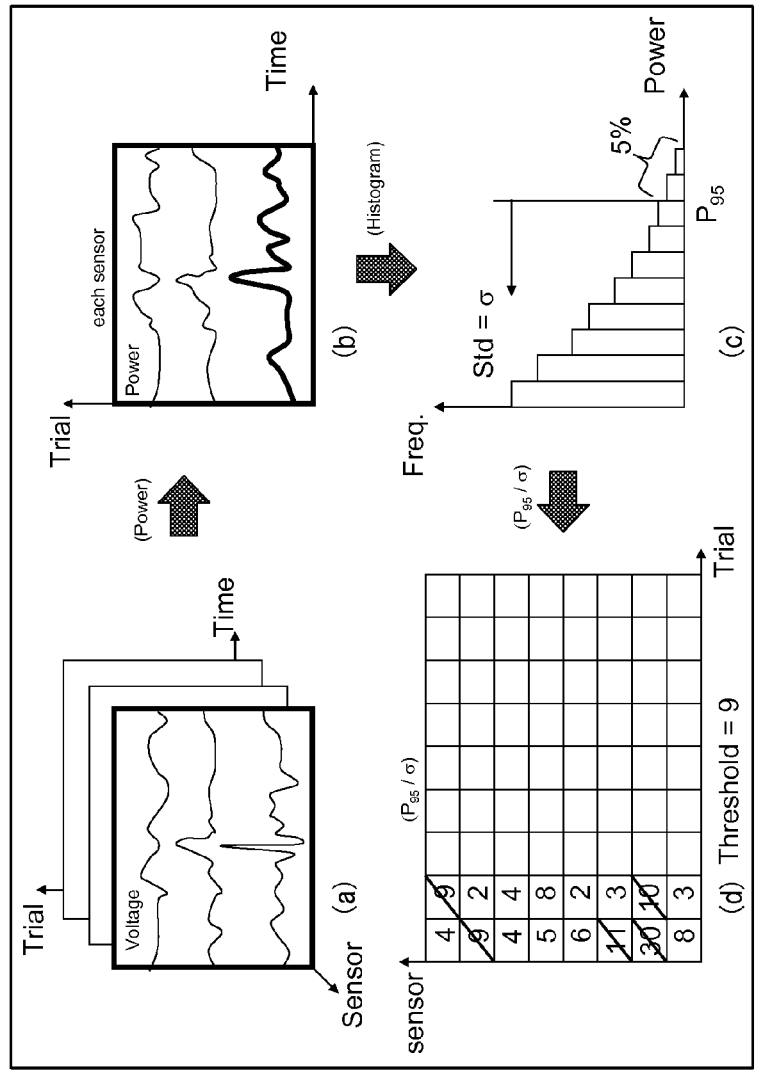
FIG. 18 is a conceptual diagram of the abnormal data removing processing in Embodiment 2.
Figure 19:
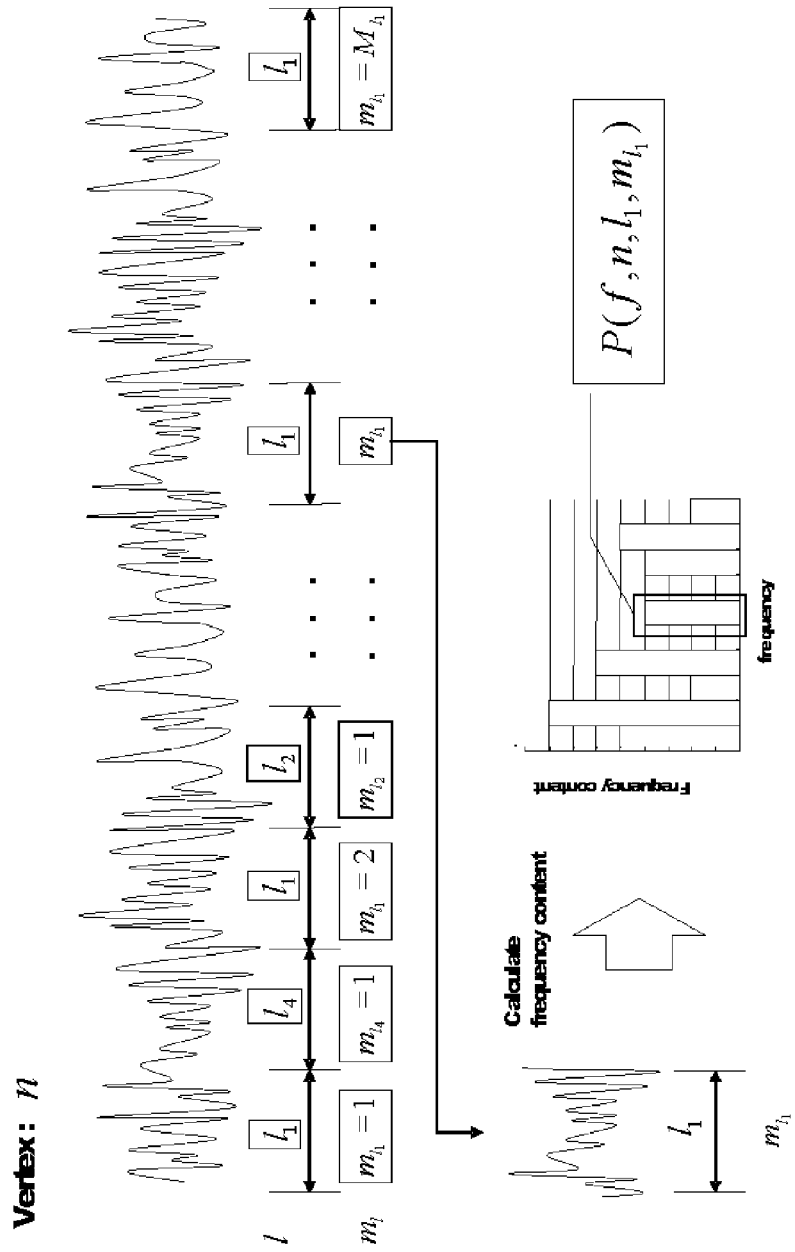
FIG. 19 is a schematic diagram of a procedure of current estimation at current source in Embodiment 2.
Figure 20:
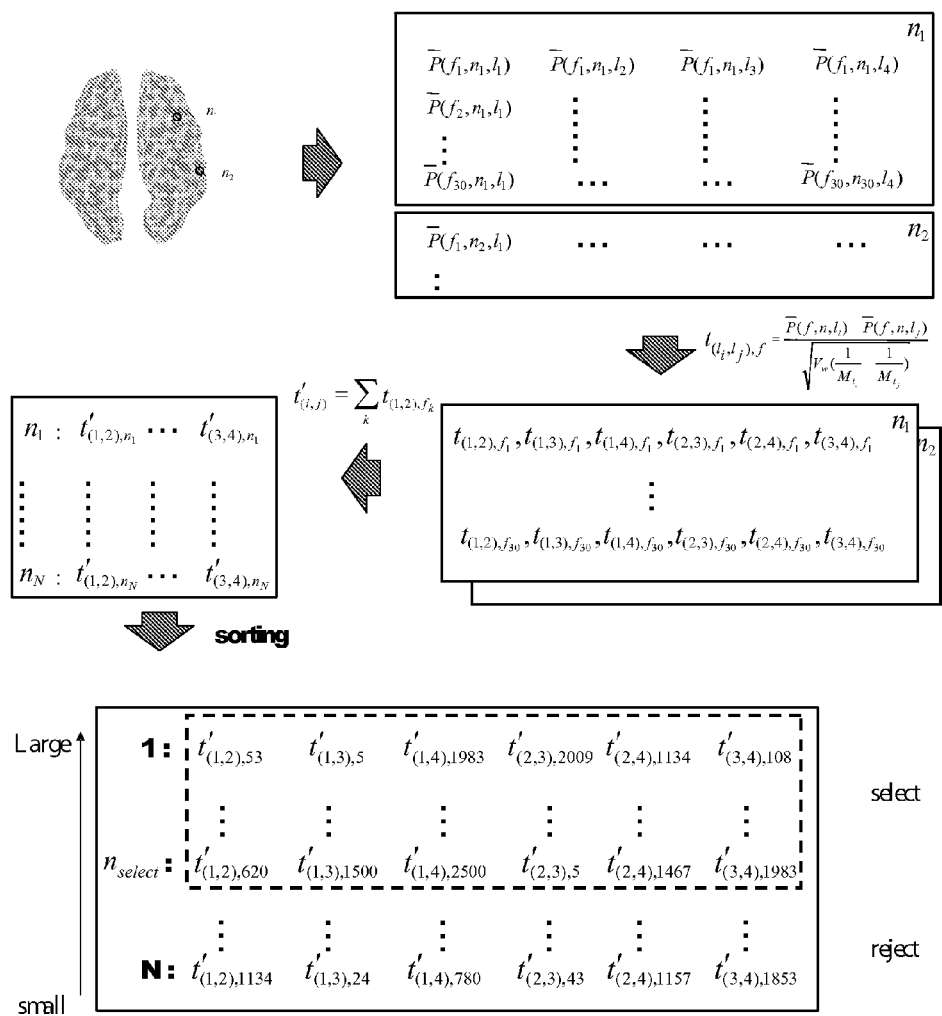
FIG. 20 is a schematic diagram of a procedure of current estimation at current source in Embodiment 2.
Figure 21:
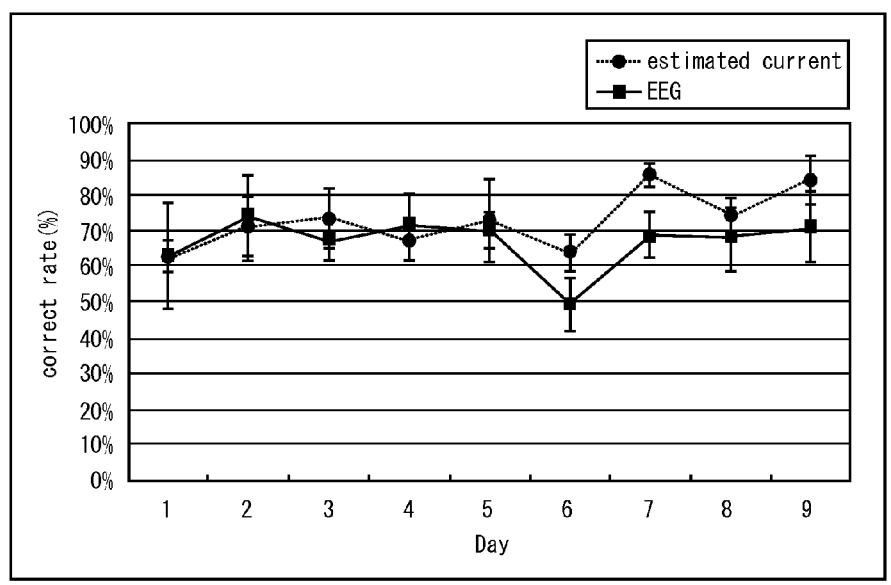
FIG. 21 shows experimental results for Subject 1 in Embodiment 2.
Figure 23:
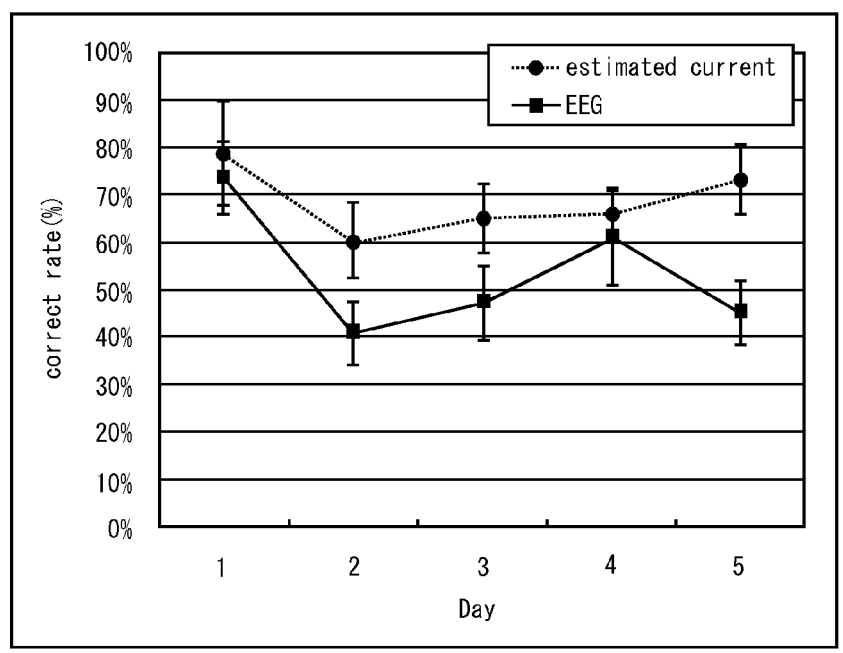
FIG. 23 shows experimental results for Subject 2 in Embodiment 2.
Figure 25:
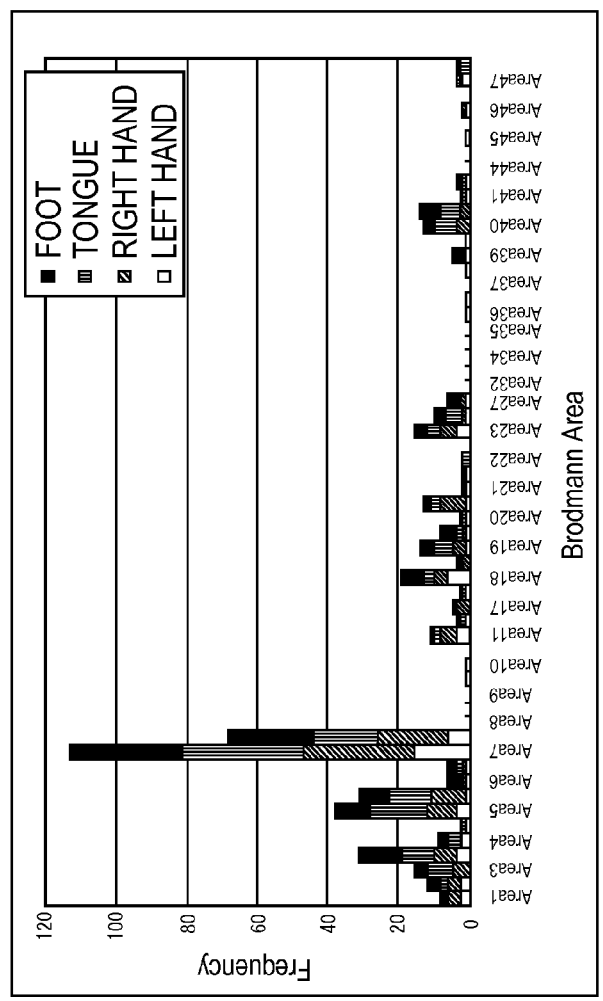
FIG. 25 shows current sources finally remained in Embodiment 2.
Figure 26:
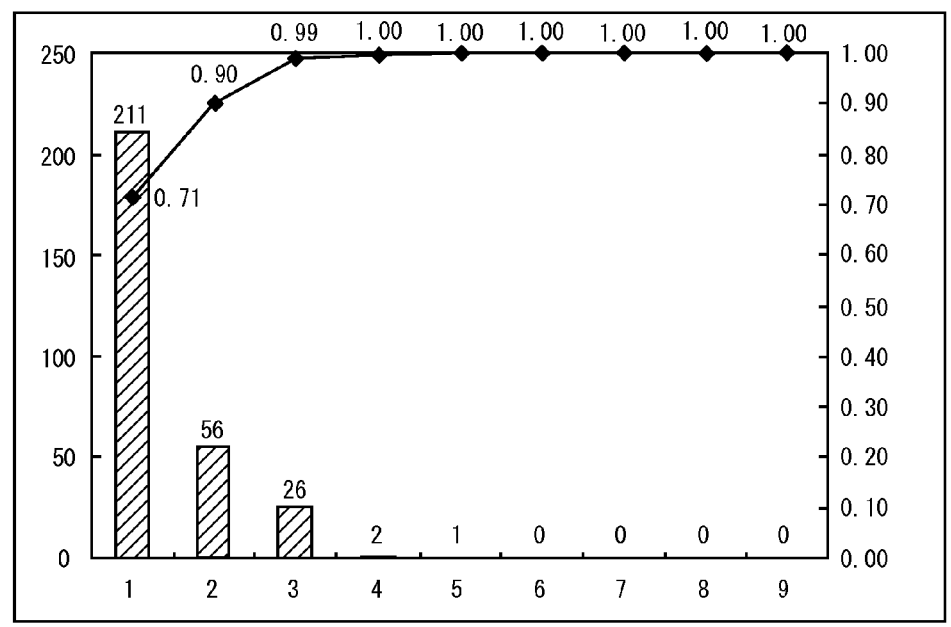
FIG. 26 shows current sources that contributed to determination and serve as feature amounts, in Embodiment 2.
Figure 27:
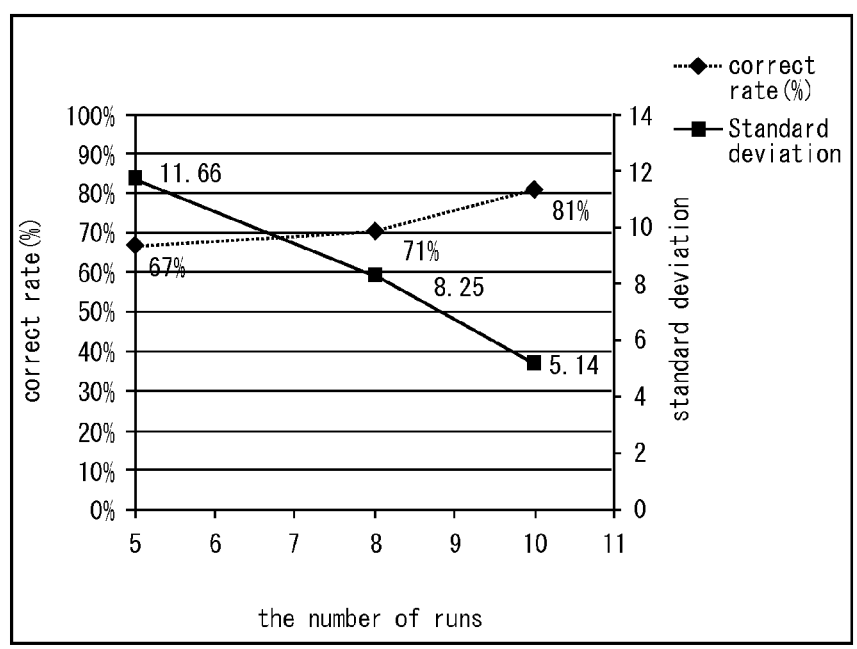
FIG. 27 shows determination results in Embodiment 2.
Figure 29:
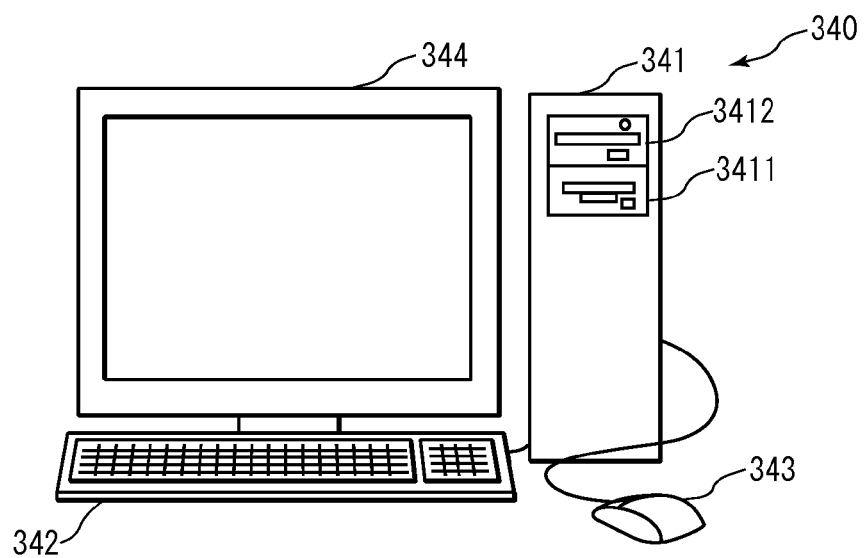
FIG. 29 is a schematic diagram illustrating a computer system in Embodiment 2.
Figure 30:
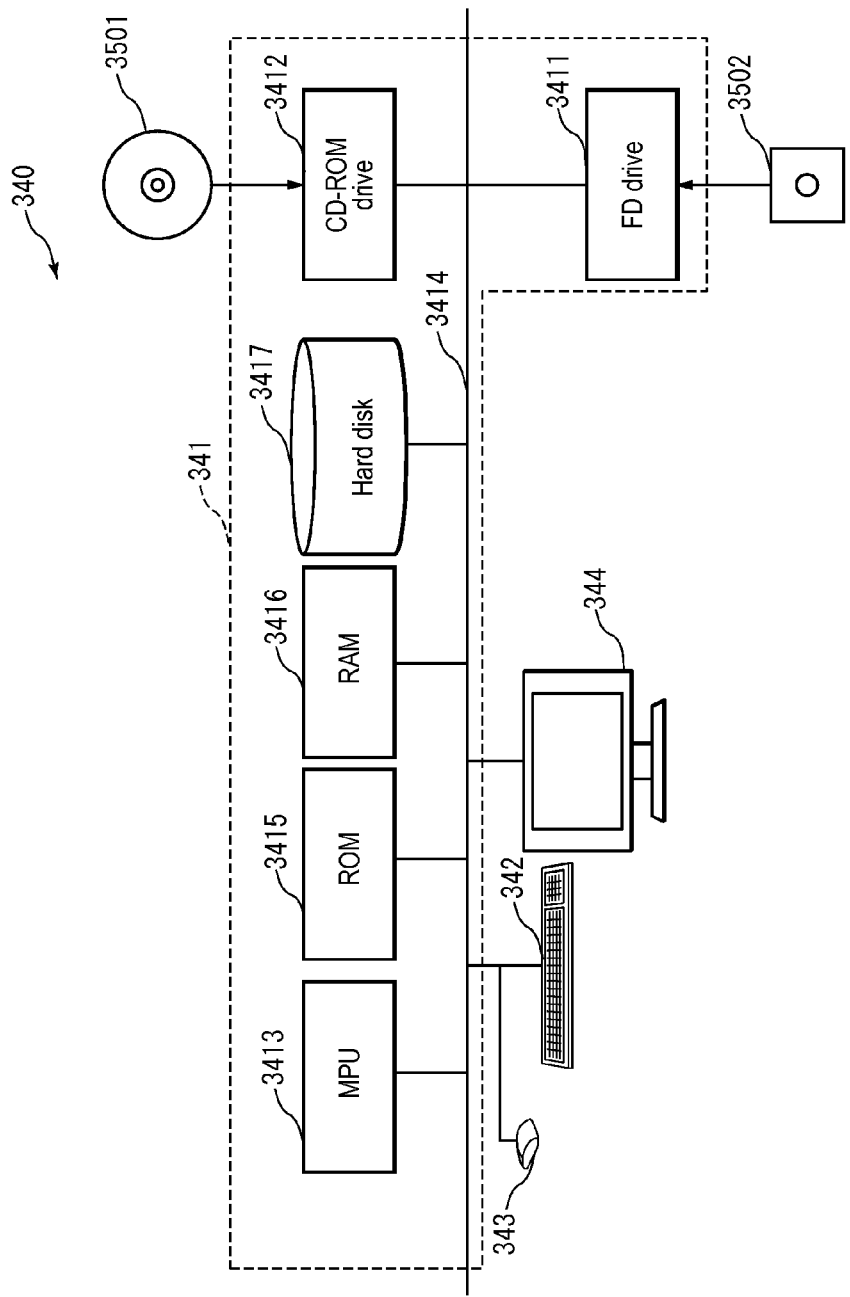
FIG. 30 is a block diagram of the computer system in Embodiment 2.

The invention claimed is:

1. A brain information output apparatus, comprising:
an intention determination information storage unit which stores two or more pieces of intention determination information, each piece of intention determination information including i) an intention identifier that is information for identifying an intention of a user, and ii) two or more types of learning feature amount groups that respectively derive from two or more types of first learning data, each type of the first learning data being data of a brain activity acquired from the outside of the cranium of a user when the user performs a trial, which is a series of actions, according to an intention identified by the intention identifier, wherein each learning feature amount group includes one or more feature amounts extracted from second learning data that is obtained by converting the first learning data into intracerebral brain activity data;
a first brain activity data acquiring unit, which acquires two or more types of first brain activity data, which is data of a brain activity, from the outside of the cranium of a user;
a second brain activity data acquiring unit, which converts each of the two or more types of first brain activity data acquired from the outside of the cranium of a user to intracerebral brain activity data, and acquires two or more types of second brain activity data
a feature amount group acquiring unit, which performs signal processing on each of the two or more types of second brain activity data, and acquires input feature amount groups including one or more feature amounts; and
an intention identifier acquiring unit, which comprises:
a probability calculation section, which, for each type of the learning feature amount groups included in the intention determination information, and for each intention identifier, calculates a probability that the input feature amount group acquired by the feature amount group acquiring unit corresponds to each of two or more intention identifiers included in the two or more pieces of intention determination information in the intention determination information storage unit, using the two or more types of learning feature amount groups, for each of the two or more intention identifiers, and which also calculates an ultimate probability for each intention identifier by using the probabilities calculated; and
an intention identifier acquiring section, which acquires an intention identifier that corresponds to a largest probability of the ultimate probabilities obtained for each of the intention identifiers calculated by the probability calculation section.

2. The brain information output apparatus according to claim 1, further comprising:
a first learning data acquiring unit that acquires, when a user performs a trial, which is a series of actions, according to one intention, two or more types of first learning data, which is time-series data indicating a brain activity, from the outside of the cranium of the user using one or more sensors, for each of the sensors;
an abnormal data removing unit which acquires one or more partial learning data sets from the first learning data, acquires a feature value for each of the partial learning data sets, determines whether the partial learning data is normal or abnormal using the feature values, removes partial learning data determined to be abnormal from the learning data, and acquires normal learning data;
a second learning data acquiring unit that converts the normal data learning data to the data of an intracerebral brain activity, and acquires second learning data;
a learning feature amount group acquiring unit that acquires, from the second learning data, a learning feature amount group including one or more features amounts; and
an intention determination information accumulation unit that accumulates, in the intention determination information storage unit, intention determination information including the second learning feature amount group and the intention identifier for identifying the one intention.

3. The brain information output apparatus according to claim 2, wherein
the abnormal data removing unit comprises an abnormal trial removing section and an abnormal sensor removing section; wherein
the abnormal trial removing section acquires the feature value of partial learning data of each trial, and determines whether partial learning data is normal or abnormal using the corresponding feature value, removes partial learning data determined to be abnormal from the learning data, and acquires normal learning data; and
the abnormal sensor removing section acquires the feature value of partial learning data of each sensor, and determines whether partial learning data is normal or abnormal using the corresponding feature value, removes partial learning data determined to be abnormal from learning data, and acquires normal learning data.

4. The brain information output apparatus according to claim 1, wherein the first learning data and the first brain activity data comprise brain wave data.

5. The brain information output apparatus according to claim 1, wherein the two or more types of first learning data comprises brain wave data and near-infrared spectrophotometry (NIRS) data.

6. A system comprising: a robot; and a brain information apparatus according to claim 1.

7. A method comprising the steps of:
storing two or more pieces of intention determination information in an intention determination information storage unit, wherein each piece of intention determination information includes i) an intention identifier that is information for identifying an intention of a user, and
ii) two or more types of learning feature amount groups that respectively derive from two or more types of first learning data, each type of the first learning data being data of a brain activity acquired from the outside of the cranium of a user when the user performs a trial, which is a series of actions, according to an intention identified by the intention identifier, wherein each learning feature amount group includes one or more feature amounts extracted from second learning data that is obtained by converting the first learning data into intracerebral brain activity data;

acquiring two or more types of first brain activity data from outside of the cranium of a user in a first brain activity data acquiring unit;

converting each of the two or more types of first brain activity data to intracerebral brain activity in a second brain activity data acquiring unit, thereby acquiring two or more types of second brain activity data; and acquiring an intention identifier in an intention identifier acquiring unit, wherein the intention identifier acquiring unit comprises:

a probability calculation section, which, for each type of the learning feature amount groups included in the intention determination information, and for each intention identifier, calculates a probability that the input feature amount group acquired by the feature amount group acquiring unit corresponds to each of two or more intention identifiers included in the two or more pieces of intention determination information in the intention determination information storage unit, using the two or more types of learning feature amount groups, for each of the two or more intention identifiers, and which also calculates an ultimate probability for each intention identifier by using the probabilities calculated; and an intention identifier acquiring section, which acquires an intention identifier that corresponds to a largest probability of the ultimate probabilities obtained for each of the intention identifiers calculated by the probability calculation section.

* * * * *